United States Patent [19]

Westphal et al.

[11] 4,036,632
[45] * July 19, 1977

[54] HERBICIDAL AGENTS

[75] Inventors: Kurt Westphal, Wuppertal-Vohwinkel; Werner Meiser, Wuppertal-Elberfeld; Ludwig Eue, Cologne-Stammheim; Helmuth Hack, Cologne-Buchheim, all of Germany

[73] Assignee: Bayer Aktiengesellschaft, Leverkusen, Germany

[*] Notice: The portion of the term of this patent subsequent to June 8, 1993, has been disclaimed.

[21] Appl. No.: 650,576

[22] Filed: Jan. 19, 1976

Related U.S. Application Data

[60] Division of Ser. No. 526,663, Nov. 25, 1974, Pat. No. 3,966,715, which is a continuation of Ser. No. 120,713, March 3, 1971, abandoned, which is a continuation-in-part of Ser. No. 6,647, Jan. 28, 1970, Pat. No. 3,671,523, which is a continuation-in-part of Ser. No. 630,225, April 12, 1967, Pat. No. 3,961,936.

[30] Foreign Application Priority Data

Nov. 14, 1966 Germany .............................. 1542873

[51] Int. Cl.² ............................................... A01N 9/22
[52] U.S. Cl. ......................................................... 71/93
[58] Field of Search ............................................. 71/93

[56] References Cited

U.S. PATENT DOCUMENTS

| | | | |
|---|---|---|---|
| 3,905,801 | 9/1975 | Fawzi | 71/93 |
| 3,961,936 | 6/1976 | Westphal et al. | 71/93 |

*Primary Examiner*—Glennon H. Hollrah
*Attorney, Agent, or Firm*—Burgess, Dinklage & Sprung

[57] ABSTRACT

3-[Hydrogen-, (unsubstituted and halo, amino, alkylamino, nitro, alkyl, alkoxy, alkylmercapto, aryloxy and/or haloarylmercapto, -substituted) aliphatic-, cycloaliphatic-, araliphatic-, aryl-, or N-heterocyclic- or O-alkanoyl-, -substituted oxy, mercapto or amino]- 4-[amino; mono and di (unsubstituted and cyano, hydroxy and/or halo, -substituted) alkyl- and/or alkanoyl-, -amino; N- (unsubstituted and cyclo- alkyl, aryl, haloaryl, alkaryl, alkoxy aryl, nitroaryl, halo-nitro-aryl, aryl-alkenyl, heterocyclic and/or nitro-heterocyclic- -substituted) alkylidene-amino or cycloalkylidene- -amino; or N-heterocyclic]-6-[(unsubstituted and halo, nitro, carbo lower alkoxy, alkyl, alkoxy, aryloxy, alkylmercapto, arylmercapto and/or aralkylmercapto, -substituted) aliphatic, cycloaliphatic, araliphatic, aryl, heterocyclic or heterocyclicalkyl]-1,2,4-triazine-5-ones, which possess herbicidal properties, and which may be produced by conventional methods; herbicidal compositions containing such compounds; and methods of using such compounds as herbicides.

2 Claims, No Drawings

HERBICIDAL AGENTS

This application is a division of application Ser. No. 526,663, filed Nov. 25, 1974, now U.S. Pat. No. 3,966,715, which was a continuation of application Ser. No. 120,713, filed Mar. 3, 1971, now abandoned, which was a continuation-in-part of copending U.S. application Ser. No. 6,647, filed Jan. 28, 1970, now U.S. Pat. No. 3,671,523, which in turn is a continuation-in-part of copending U.S. application Ser. No. 630,225, filed Apr. 12, 1967, now U.S. Pat. No. 3,961,936.

The present invention relates to and has for its objects the provision for particular substituted 4-amino-1,2,4-triazine-5-ones, some of which are known, which possess valuable, especially selective, herbicidal properties, active compositions in the form of mixtures thereof with solid and liquid dispersible carrier vehicles, and methods for their preparation and use, especially for combatting weeds, undesired plants, and the like; with other and further objects of this invention becoming apparent from a study of the within specification and accompanying examples.

It is known that 1,3,5-triazines can be used for the control of weeds (see Belgian Pat. No. 540,590). In this group of active compounds, 2,6-di-(othylamino)-4-chloro-1,3,5-triazine (A) has attained a considerably practical significance.

It has now been found, in accordance with the present invention, that the particular 4-amino-1,2,4-triazine-5-ones having the formula

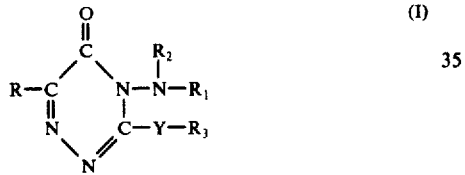

in which

R is selected from the group consisting of aliphatic having 1-18 carbon atoms, cycloaliphatic having 5-10 ring carbon atoms, araliphatic having 6-10 ring carbon atoms in the corresponding aryl moiety and 1-4 carbon atoms in the aliphatic moiety, aryl having 6-10 ring carbon atoms, heterocyclic having 5-6 ring members with at least one hetero linking atom selected from the group consisting of O, N, S and mixtures of such hereto atoms, heterocyclic-lower alkyl in which the heterocyclic moiety has 5-6 ring members with at least one hetero linking atom selected from the group consisting of O, N, S and mixtures of such hetero atoms, and such aliphatic, cycloaliphatic, araliphatic, aryl, heterocyclic and heterocyclic-lower alkyl, respectively, which is substituted with at least one substituent selected from the group consisting of halo, nitro, carbo lower alkoxy, lower alkyl, lower alkoxy, aryloxy having 6-10 ring carbon atoms, lowr alkylmercapto, arylmercapto having 6-10 ring carbon atoms, aryl-lower alkylmercapto having 6-10 ring carbon atoms in the aryl moiety, and mixtures of such substituents;

$R_1$ and $R_2$ each respectively is selected from the group consisting of hydrogen, alkyl having 1-12 carbon atoms, alkanoyl having 1-6 carbon atoms, and such alkyl and alkanoyl, respectively, which is substituted with at least one substituent selected from the group consisting of cyano, hydroxy, halo, and mixtures of such substituents, with the proviso that $R_1$ and $R_2$ when taken together represent alkylidene having 1-12 carbon atoms, cycloalkylidene having 5-8 ring carbon atoms, and such alkylidene and cycloalkylidene, respectively, which is substituted with at least one substituent selected from the group consisting of cycloalkyl having 5-8 ring carbon atoms, aryl having 6-10 ring carbon atoms, haloaryl having 6-10 ring carbon atoms, lower alkyl aryl having 6-10 ring carbon atoms in the aryl moiety, lower alkoxy aryl having 6-10 ring carbon atoms in the aryl moiety, nitroaryl having 6-10 ring carbon atoms, halo-nitroaryl having 6-10 ring carbon atoms, aryl-lower alkenyl having 6-10 carbon atoms in the aryl moiety, heterocyclic having 5-6 ring members with at least one hetero linking atom selected from the group consisting of O, N, S and mixtures of such hetero atoms, nitro-heterocyclic having 5-6 ring members with at least one hetero linking atom selected from the group consisting of O, N, S and mixtures of such hetero atoms, and mixtures of such substituents, and with the further proviso that $R_1$ and $R_2$ when taken together with the adjacent N atom represent N-containing heterocyclic having 5-6 ring members;

Y is selected from the group consisting of O, S and

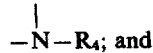

$R_3$ and $R_4$ each respectively is selected from the group consisting of hydrogen, aliphatic having 1-18 carbon atoms, cycloaliphatic having 5-8 ring carbon atoms, araliphatic having 6-10 carbon atoms in the corresponding aryl moiety and 1-4 carbon atoms in the aliphatic moiety, aryl having 6-10 ring carbon atoms, and such aliphatic, cycloaliphatic, araliphatic and aryl, respectively, which is substituted with at least one substituent selected from the group consisting of halo, amino, lowr alkyl substituted amino, nitro, lower alkyl, lower alkoxy, lower alkylmercapto, aryloxy having 6-10 ring carbon atoms, haloarylmercapto having 6-10 carbon atoms, and mixtures of such substituents, with the provisio that $R_3$ and $R_4$ when taken together with the adjacent N atom represent N-containing heterocyclic having 5-6 ring members; and with the further proviso that when Y is O then $R_3$ may also be a lower alkanoyl;

exhibit strong herbicial properties.

It is very surprising that the particular active compounds usable according to the present invention not only show a stronger herbicial activity than the known triazines in pre-emergence application but also show a good herbicial activity when used according to the post-emergence method. Apart from this, the instant compounds also show marked select herbicial properties (see Examples 1 and 2 hereinbelow).

Some of the 1,2,4-triazine-5-ones usable according to the present invention are already known from the literature (cf. Chemische Berichte 97, 2173–2178, 1964).

The following compounds are new: 1,2,4-triazine-5-ones of the above formula (I) wherein correspondingly:

a. R, $R_1$, $R_2$ and $R_3$ are the same as defined above, and Y is oxygen, provided that $R_3$ may also be said alkanoyl;

or b. R is aliphatic hydrocarbon having at least two, or at least three, or at least four, or at least five, or at least six, or more (i.e. 2–18 or 3–18 or 4–18 or 5–18 or 6–18, etc.), carbon atoms, or said cycloaliphatic hydrocarbon, araliphatic hydrocarbon, heterocyclic or heterocyclic-alkyl which, in each case, may be substituted with one or more of said halo, nitro, carboalkoxy, alkyl, alkoxy, aryloxy, alkylmercapto, arylmercapto and/or aryl-alkylmercapto, or R is said aryl which is substituted with one or more of said halo, nitro, carboalkoxy, alkyl, alkoxy, aryloxy, alkylmercapto, arylmercapto and/or aryl-alkylmercapto, $R_1$, $R_2$ and $R_3$ are the same as defined above, and Y is sulfur; or c. R, $R_1$ and $R_2$ are the same as defined above, $R_3$ is aliphatic hydrocarbon having at least two, or at least three, or at least four, or at least five, or at least six, or more (i.e. 2–18 or 3–18 or 4–18 or 5–18 or 6–18, etc.), carbon atoms, or said cycloaliphatic hydrocarbon, araliphatic hydrocarbon or aryl which, in each case, may be substituted with one or more of said halo, amino, alkyl substituted amino, nitro, alkyl, alkoxy, alkylmercapto aryloxy and/or haloarylmercapto, and Y is sulfur; or d. R and $R_3$ are the same as defined above, $R_1$ and $R_2$ each individually is said alkyl or acyl, i.e. alkanoyl, which may be substituted with one or more of said cyano, hydroxy and/or halo, or $R_1$ and $R_2$ taken jointly represent said alkylidene or cycloalkylidene, which, in each case, may be substituted with one or more of said cycloalkyl, aryl, haloaryl, ikylaryl, alkoxy aryl, nitroaryl, halonitro-aryl, aryl-alkenyl, heterocyclic and/or nitro-hetercyclic, or preferably represent alkylidene having at least two, or at least three, or at least four, or at least five, or at least six, or more (i.e. 2–18 or 3–18 or 4–18 or 5–18 or 6–18 or 6–18, ect.), carbon atoms which is substituted with said aryl, or preferaby represent said unsubstituted cycloalkylidene, or $R_1$ and $R_2$, together with the adjacent nitrogen atom, represent said heterocyclic, and Y is sulfur; or e. R is aliphatic hydrocarbon having at least two, or at least three, or at least four, or at least five, or at least six, or more, (i.e. 2–18, 3–18, 4–18, 5–18, 6–18, ect.), carbon atoms, or said cycloaliphatic hydrocarbon, araliphatic hydrocarbon, heterocyclic or heterocyclic-alkyl which, in each case, may be substituted with one or more of said halo, nitro, carboalkoxy, alkyl, alkoxy, aryloxy, alkylmercapto, arylmercapto and/or aryl-alkylmercapto, or R is said aryl which is substituted with one or more of said halo, nitro, carboalkoxy, alkyl, alkoxy, aryloxy, alkylmercapto, arylmercapto and/or aryl-alkylmercapto, $R_1$, $R_2$, $R_3$ and $R_4$ are the same as defined above, and Y is —$NR_4$; or f. R, $R_3$ and $R_4$ are the same as defined above, $R_1$ $R_2$ each individually is said alkyl or acyl, i.e., alkanoyl, which may be substituted with one or more of said cyano, hydroxy and/or halo, or $R_1$ and $R_2$ taken jointly represent said alkylidene or cycloalkylidene, which, in each case, may be substituted with one or more of said cycloalkyl, aryl, haloaryl, alkylaryl, alkoxy aryl, nitroaryl, halo-nitro-aryl, aryl-alkenyl, heterocyclic and/or nitro-heterocyclic, or preferably represent alkylidene having at least two, or at least three, or at least four, or at least five, or at least six, or more (i.e. 2–18 or 3–18 or 4–18 or 5–18 or 6–18, etc.), carbon atoms which is substituted with said aryl, or preferably represent said unsubstituted cycloalkylidene, or $R_1$ and $R_2$, together with the adjacent nitrogen atom, represent said heterocyclic, and Y is —$NR_4$; or g. R, $R_1$ and $R_2$ are the same as defined above, $R_3$ is hydrogen and $R_4$ is unsubstituted alihatic hydrocarbon having up to three carbon atoms, or said substituted aliphatic hydrocarbon, substituted or unsubstituted cycloalihatic hydrocarbon, substituted araliphatic or substituted aryl, or $R_3$ and $R_4$ each individually is said substituted or unsubstituted aliphatic hydrocarbon, cycloaliphatic hydrocarbon, araliphatic hydrocarbon or aryl, or $R_3$ and $R_4$, together with the adjacent nitrogen atom, represent oxygen-free N-containing heterocyclic having 5–6 ring members which may be substituted with one or more halo, amino, alkyl substituted amino, nitro, alkyl, alkoxy, alkylmercapto, aryloxy, and/or halo arylmercapto, and Y is —$NR_4$.

The instant new triazinones can be prepared according to the customary methods in the same manner as the known triazinones [see for example Berichte 97, 2173–2178 (1964)].

Advantageously, the instant triazinones influence plant growth and can be used as defoliants, desiccants or herbicides and in particular as weed-killers.

By defoliants and desiccants are meant the customary harvest auxiliaries which are used for removing the leaves from and for drying out the green portions of plants before bringing in the harvest.

By weeds are meant in the widest sense all plants which grow in places where they are undesired.

The instant triazinones can be used as total herbicides for the destruction of weeds, and also as selective herbicides for the destruction of weeds in connection with the cultivation of specific agricultural crops. Whether the instant triazinones act as total herbicides or as selective herbicides depends largely on the concentration thereof which is used as the artisan aware of the present invention will appreciate. Examples of crops for which the triazinones of the instant invention are suitable are cereals (such as oats, barely, rice, maize and in particular wheat), cotton, carrots, snap bean, peas, potatoes, beets, and the like.

As weeds which can be destroyed in accordance with the present invention, there may be mentioned as illustrative examples: dicotyledons, such as mustard (Sinapis), cress (Lepidium), cleaver (Galium), common chickweed (Stellaris), camomile (Matricaria), smallflower Galinsoga (Galinsoga), fathen (Chenopodium), burning nettle (Urtica), groundsel (Senecio); monocotyledons, such as timothy (Phleum), meadow grass (Poa), fescue grass (Festuca), goosegrass (Eleusine), foxtail (Setaria), ryegrass (Lolium), brome grass (Bromus), barnyard grass (Echinochloa), and the like.

The active compounds according to the instant invention can be utilized, if desired, in the form of the usual formulations or compositions with dispersible carrier vehicles, such as solutions, emulsions,, suspensions, emulsifiable concentrates, spray powders, pastes, soluble powders, dusting agents, granulates, etc. These are prepared in known manner, for instance by extending the active agents with dispersible liquid diluent carriers and/or dispersible solid carriers optionally with the use of carrier vehicle assistants, e.g., surface-active agents, including emulsifying agents and/or dispersing agents, whereby for example, in the case where water is used as diluent, organic solvents may be added as auxiliary solvents (see Agricultural Chemicals, March 1960, pp. 35–38). The following may be chiefly considered for use as carrier vehicles with the use of carrier vehicle assistants, e.g., surface-active agents, including emulsifying agents and/or dispersing agents, whereby for example, in the case where water is used as diluent, organic solvents may be added as auxiliary solvents (see Agricultural Chemicals, March 1960, pp. 35–38). The following may be chiefly considered for use as carrier vehicles for this purpose: dispersible liquid diluent carriers, such as aromatic hydrocarbons (for instance, benzene, toluene, xylene, etc.), halogenated, especially chlorinated, aromatic hydrocarbons (for instance, chlorobenzenes), paraffins (for instance petroleum fractions). chlorinated aliphatic hydrocarbons (for instance, methylene chloride, etc.), alcohols (for instance, methanol, ethanol, propanol, butanol, etc.), ethers, ether-alcohols (for instance, glycol monomethyl ether, etc.), amines (for instance, ethanolamine, etc.), amides (for instance dimethyl formamide, etc), sulfoxides (for instance, dimethyl sulfoxide, etc.), ketones (for instance, acetone, etc.), and water; as well as dispersible finely divided solid carriers, such as ground natural minerals (for instance, kaolins, alumina, silica, chalk, i.e., calcium carbonate, talc, kieselguhr, etc.), and ground synthetic minerals (for instance, highly dispersed silicic acid, silicates, e.g., alkali silicates, etc.); whereas the following may be chiefly considered for use as carrier vehicle assistants, e.g., surface-active agents, for this purpose: emulsifying agents, such as nonionic and anionic emulsifying agents (for instance, polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, etc.); and dispersing agents, such as lignin, sulfite waste liquors, methyl cellulose, etc.

As will be appreciated by the artisan, the active compounds according to the instant invention may be present in such formulations or compositions in the form of mixtures with one another and with other known active substances such as for example known herbicides including ureas, other triazines, uracils, aminotriazole, phenoxy carboxylic acids, benzoic acid, picolinic acid, and the like, if desired.

The substances according to the invention may be employed, therefore, by themselves as the artisan will appreciate, in the form of their composition with solid or liquid dispersible carrier vehicles or other known compatible active agents, or in the form of particular dosage preparations for specific application made therefrom, such as solutions, emulsions, suspensions, powders, pastes, and granulates which are thus ready for use.

As concerns commercially marketed preparations, these generally contemplate carrier compositions mixtures in which the active compound is present in an amount substantially between about 0.1 and 95% by weight, and preferably 0.5 and 90% by weight, of the mixture, whereas carrier compositions mixtures suitable for direct application or field application generally contemplate those in which the active compound is present in an amount substantially between about 0.001 and 1.0%, preferably 0.005 and 0.5%, by weight of the mixture. Thus, the present invention contemplates over-all compositions which comprise mixtures of a dispersible carrier vehicle such as a dispersible carrier solid, or a dispersible carrier liquid preferably including a carrier vehicle assistant e.g., a surface-active agent, such as an emulsifying agent and/or a dispersing agent, and an amount of the active compound which is effective for the purpose in question and which is generally between about 0.001 and 95% by weight of the mixture. Specifically, the active compound may be applied to a surface area, such as in pre-emergence use, in concentrations substantially between about 0.5 and 20 kg per hectare, preferably between about 1 and 10 kg per hectare, although it will be appreciated that in connection with the pre-emergence use of the instant compounds, as well as the post-emergence use thereof, the concentration may be varied within a fairly wide range. However, generally the post-emergence range of concentration will be between about 0.001 and 95%, preferably between about 0.005 and 95%, by weight of the mixture as aforesaid, while the pre-emergence range will be between about 0.5 and 20, preferably between about 1 and 10, kg per hectare, as aforesaid.

Furthermore, the present invention contemplates methods of selectively controlling or combatting undesired plants, e.g., weeds and the like, which comprise applying to at least one of (a) such weeds and (b) their habitat, a herbicidally effective amount of the particular active compound of the invention alone or together with a carrier vehicle as noted above. The instant formulations or compositions are applied in the usual manner, for example, by spraying, atomizing, scattering, dusting, watering, sprinkling, dispersing, and the like, whether for pre-emergence application to the soil or post-emergence application to the weeds.

The following Examples are given for the purpose of illustrating, without limiting, the utility of the instant invention.

EXAMPLE 1

Pre-emergence test

Solvent: 5 parts by weight acetone
Emulsifier: 1 part by weight benzyloxypolyglycol ether To produce a suitable preparation of the particular active compound, 1 part by weight of such active compound is mixed with the stated amount of solvent, the stated amount of emulsifier is then added and the resulting concentrate is thereafter diluted with water to the desired final concentration.

Seeds of the test plants are sown in normal soil and, after 24 hours, watered with the preparation of the given active compound. It is expedient to keep constant the amount of water per unit area. The concentration of the particular active compound in the preparation is of no importance, only the amount of active compound applied per unit area being decisive. After 3 weeks, the degree of damage to the test plants is determined and characterized by the values 0–5, which have the following meaning:

0    no effect
1    slight damage or delay in growth
2    marked damage or inhibition of growth 3    heavy damage and only deficient development or only 50% emerged 4 plants partially destroyed after germination or only 25% emerged
5 plants completely dead or not emerged.

The particular active compounds, the amount applied and the results obtained can be seen from the following Table 1:

Table 1

Pre-emergence test

| | Active compound | Active compound used in kg/hectare | Oats | Wheat | Cotton | Sinapis | Chenopodium | Galinsoga | Echinochloa | Avena fatua |
|---|---|---|---|---|---|---|---|---|---|---|
| (A) | Cl-triazine (H₅C₂-NH-C=N-C(Cl)=N-C=N-NH-C₂H₅) (known from Belgian Patent 540,590) | 5<br>2.5<br>1.25 | 4<br>4<br>3 | 4<br>3<br>2 | 5<br>4<br>3 | 5<br>5<br>5 | 5<br>5<br>5 | 5<br>5<br>5 | 3–4<br>3<br>2 | 5<br>4<br>3 |
| (1a) | phenyl-C(=O)-C(N-NH₂)=N-N=C-SCH₃ | 5<br>2.5<br>1.25 | 5<br>5<br>3 | 5<br>5<br>2 | 3<br>1<br>0 | 5<br>5<br>5 | 5<br>5<br>5 | 5<br>5<br>5 | 5<br>5<br>4–5 | 5<br>5<br>4 |

Pre-emergence test

| | Active compound | Active compound used in kg/hectare | Oats | Wheat | Cotton | Sinapis | Chenopodium | Galinsoga | Echinochloa |
|---|---|---|---|---|---|---|---|---|---|
| (2) | cyclohexyl-C(=O)-C(N-NH₂)=N-N=C-SCH₃ (new compound) | 5<br>2.5<br>1.25 | 5<br>5<br>4–5 | 5<br>5<br>4–5 | 5<br>5<br>5 | 5<br>5<br>5 | 5<br>5<br>5 | 5<br>5<br>5 | 5<br>5<br>5 |
| (3) | phenyl-C(=O)-C(N-NH₂)=N-N=C-SC₂H₅ (new compound) | 10<br>5<br>2.5 | 3<br>2<br>1 | 1<br>0<br>0 | 0<br>0<br>0 | 5<br>5<br>4 | 5<br>5<br>5 | 5<br>5<br>5 | 5<br>4<br>3 |

The following instant compounds having the appropriate substituents designated in Table 1A for Formula (I) act in the same way was active compound (1a):

Table 1A

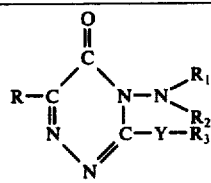

(I)

| | R | $R_1$ | $R_2$ | $R_3$ | $R_4$ | Y | |
|---|---|---|---|---|---|---|---|
| (4) | benzyl (–CH₂–phenyl) | H | H | –CH₃ | | S | new compound |
| (5) | 2-furyl-methyl | H | H | –CH₃ | | S | new compound |
| (6) | 2-furyl-phenyl | –CO–CH₃ | –COCH₃ | –CH₃ | | S | new compound |

Table 1A-continued

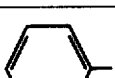

(I)

| | R | $R_1$ | $R_2$ | $R_3$ | $R_4$ | Y | |
|---|---|---|---|---|---|---|---|
| (7) |  phenyl- | H | H | $-C_2H_5$ | H | N | new compound |
| (8) |  phenyl- | $-COCH_3$ | H | $-CH_3$ | | S | new compound |
| (9) |  phenyl- | H | H | $-CH_3$ | H | N | new compound |
| (10) | 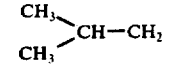 Cl—C₆H₄—CH₂— | H | H | $-CH_3$ | H | N | new compound |
| (11) | (CH₃)₂CH—CH₂— | H | H | $-CH_3$ | | S | new compound |
| (12) |  phenyl- | H | H | $-CH_2-CH_2-CH_3$ | H | N | new compound |
| (13a) |  phenyl- | H | H | $-CH_2CH_2-O-CH_2CH_2-$ | | N | |

The following instant compounds having the appropriate substituents designated in Table 1B for Formula (I) above act in the same way as active compound (2), which has a pronouncedly total-herbicidal action:

Table 1B

| | R | $R_1$ | $R_2$ | $R_3$ | $R_4$ | Y | |
|---|---|---|---|---|---|---|---|
| (14) | 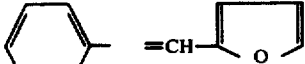 phenyl- | =CH—(furyl) | | $-CH_3$ | | S | new compound |
| (15) | 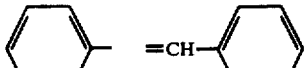 phenyl- | =CH—(phenyl) | | $-CH_3$ | | S | new compound |
| (16) |  phenyl- | H | H | $-CH_3$ | $-CH_3$ | N | new compound |
| (17) |  phenyl- | =C(CH₃)₂ | | $-CH_3$ | | S | new compound |
| (18) |  phenyl- |  =cyclohexyl | | $-CH_3$ | | S | new compound |
| (19) | 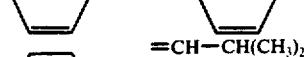 phenyl- | =CH—CH(CH₃)₂ | | $-CH_3$ | | S | new compound |

Table 1B-continued

| | R | R₁ | R₂ | R₃ | R₄ | Y | |
|---|---|---|---|---|---|---|---|
| (20) | phenyl | —CHOH—CCl₃ | H | —CH₃ | | S | new compound |
| (21) | (CH₃)₂=CH— | H | H | —CH₃ | | S | new compound |
| (22) | C₂H₅— | H | H | —CH₃ | | S | new compound |
| (23) | iso-C₅H₁₁— | H | H | —CH₃ | | S | new compound |
| (24) | C₆H₁₃n— | H | H | —CH₃ | | S | new compound |

The following instant compounds having the appropriate substituents designated in Table 1C for Formula (I) above act in the same way as active compound (3), which exhibits selectively herbicidal action in wheat and cotton:

| | R | R₁ | R₂ | R₃ | R₄ | Y | |
|---|---|---|---|---|---|---|---|
| (25) | phenyl | H | H | —CH₂—CH₂\\CH₂/—CH₂—CH₂ (piperidino) | | N | new compound |
| (26) | phenyl | H | H | —CH₂—CH=CH₂ | H | N | new compound |
| (27) | phenyl | =C(CH₃)(phenyl) | | —CH₃ | | S | new compound |
| (28) | phenyl | =CH—(pyridyl) | | —CH₃ | | S | new compound |

EXAMPLE 2

Post-emergence Test

Solvent: 5 parts by weight acetone
Emulsifier: 1 parts by weight benzyloxypolyglycol ether To produce a suitable preparation of the particular active compound, 1 part by eight of such active compound is mixed with the stated amount of solvent, the stated amount of emulsifier is then added and the resulting concentrate is thereafter diluted with water to the desired final concentration.

Test plants which have a height of about 5–15 cm. are sprayed with the preparation of the given active compound until just dew moist. After 3 weeks, the degree of damage to the plants is determined and characterized by the values 0–5, which have the following meaning:

0 no effect
1 a few slightly burnt spots
2 marked damage to leaves
3 some leaves an parts of stalks partially dead
4 plant partially destroyed
5 completely dead -

The particular active compounds, their concentrations and the results obtained can be seen from the following Table 2:

Table 2

Post-emergence test

| Active compound | Concentration of active compound % | Wheat | Sinapis | Chenopodium | Stellaria | Daucus | Galinsoga | Echinochloa |
|---|---|---|---|---|---|---|---|---|
| (A') triazine structure (known from Belgian Patent 540,590) | 0.1 | 4 | 5 | 5 | 5 | 3 | 4–5 | 4 |
| | 0.05 | 2 | 5 | 5 | 5 | 1 | 4 | 3 |
| | 0.025 | 1 | 5 | 4 | 5 | 0 | 2 | 2 |
| | 0.01 | 0 | 4 | 3 | 4 | 0 | 1 | 1 |
| (1a') | 0.1 | 4 | 5 | 5 | 5 | 5 | 5 | 5 |
| | 0.05 | 2 | 5 | 5 | 5 | 5 | 5 | 5 |
| | 0.025 | 1 | 5 | 5 | 5 | 5 | 5 | 5 |
| | 0.01 | 0 | 5 | 5 | 5 | 5 | 5 | 5 |

Table 2'

Post-emergence test

| Active compound | Concentration of active compound % | Wheat | Carrots | Snap Beans | Sinapis | Chenopodium | Stellaria | Galinsoga | Echinochloa |
|---|---|---|---|---|---|---|---|---|---|
| (21') (CH₃)₂CH-C structure with N-NH₂, C-SCH₃ (new compound) | 0.05<br>0.025<br>0.01 | 5<br>5<br>4-5 | 5<br>5<br>5 | 5<br>5<br>5 | 5<br>5<br>5 | 5<br>5<br>5 | 5<br>5<br>5 | 5<br>5<br>5 | 5<br>5<br>5 |
| (28') phenyl structure with N-N=CH-pyridyl, C-SCH₃ (new compound) | 0.05<br>0.025<br>0.01 | 1<br>0<br>0 | 5<br>5<br>5 | 1<br>0<br>0 | 5<br>5<br>5 | 5<br>5<br>5 | 5<br>5<br>5 | 5<br>5<br>4 | 5<br>5<br>4 |
| (26') phenyl structure with N-NH₂, NH-CH₂-CH=CH₂ (new compound) | 0.05<br>0.025<br>0.01 | 0<br>0<br>0 | 0<br>0<br>0 | 5<br>5<br>4 | 5<br>5<br>5 | 5<br>5<br>5 | 5<br>5<br>4 | 5<br>5<br>5 | 5<br>4<br>3 |

The following instant compounds having the appropriate substituents designated in Table 2A for Formula (I) above act in the same way as active compound (1a):

Table 2A

General structure with R, R₁, R₂, R₃, R₄, Y substituents on triazinone ring.

| | R | R₁ | R₂ | R₃ | R₄ | Y | |
|---|---|---|---|---|---|---|---|
| (29a) | CH₃— | H | H | —CH₃ | | S | |
| (4') | phenyl-CH₂— | H | H | —CH₃ | | S | new compound |
| (30) | Cl-phenyl-CH₂— | H | H | —CH₃ | | S | new compound |
| (31) | phenyl | H | H | —CH₂—C≡CH | | S | new compound |
| (32) | phenyl | H | H | —CH₂—CH=CH₂ | | S | new compound |
| (7') | phenyl | H | H | —C₂H₅ | H | N | new compound |

Table 2A-continued

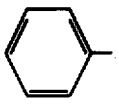

| | R | R₁ | R₂ | R₃ | R₄ | Y | |
|---|---|---|---|---|---|---|---|
| (33) | 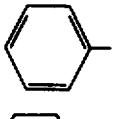 | H | H | —CH₃ | | O | new compound |
| (9') | 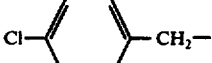 | | H | —CH₃ | H | N | new compound |
| (10') | 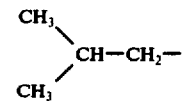 | | H | —CH₃ | H | N | new compound |
| (11') | CH₃\\CH—CH₂—/CH₃ | H | H | —CH₃ | | S | new compound |
| (34) | CH₃— | H | H | —CH₃ | H | N | new compound |
| (13a') | 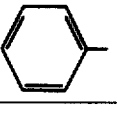 | H | H | —CH₂—CH₂—O—CH₂—CH₂— | | N | |

The following instant compounds having the appropriate substituents designated in Table 2B for Formula (I) above act in the same way as active compound (21), which has a pronouncedly total-herbicidal action:

The following instant compounds having the appropriate substituents designated in Table 20 for Formula (I) above act in the same way as active compound (28), which exhibits a pronouncedly selective-herbicidal ac-

Table 2B

| | R | R₁ | R₂ | R₃ | R₄ | Y | |
|---|---|---|---|---|---|---|---|
| (14') | 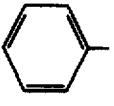 | =CH—<furan> | | —CH₃ | | S | new compound |
| (16') |  | H | H | —CH₃ | —CH₃ | N | new compound |
| (2') | 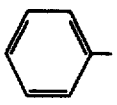 | H | H | —CH₃ | | S | new compound |
| (20') |  | —CHOH—CCl₃ | H | —CH₃ | | S | new compound |
| (23') | iso C₅H₁₁— | H | H | —CH₃ | | S | new compound | tion in snap beans and wheat:

Table 2C

| | R | R₁ | R₂ | R₃ | R₄ | Y | |
|---|---|---|---|---|---|---|---|
| (15') | 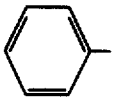 =CH—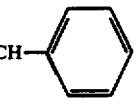 | | | —CH₃ | | S | new compound |

Table 2C-continued

| | R | R₁ | R₂ | R₃ | R₄ | Y | |
|---|---|---|---|---|---|---|---|
| (27') | phenyl- | | =C(CH₃)(C₆H₅) | —CH₃ | | S | new compound |
| (19') | phenyl- | | =CH—CH(CH₃)₂ | —CH₃ | | S | new compound |
| (22') | C₂H₅— | H | H | —CH₃ | | S | new compound |
| (24') | C₆H₁₁-n— | H | H | —CH₃ | | S | new compound |

The following instant compounds having the appropriate substituents designated in Table 2D for Formula (I) above act in the same way as active compound (26), which has a pronouncedly selective-herbicidal action in wheat and carrots:

Table 2D

| | R | R₁ | R₂ | R₃ | R₄ | Y | |
|---|---|---|---|---|---|---|---|
| (3') | phenyl- | H | H | —C₂H₅ | | S | new compound |
| (17') | phenyl- | | =C(CH₃)₂ | —CH₃ | | S | new compound |
| (18') | phenyl- | | =cyclohexyl(H) | —CH₃ | | S | new compound |
| (35) | phenyl- | | =CH—(furyl)—NO₂ | —CH₃ | | S | new compound |

EXAMPLE 3

Defolaint Test

There is prepared, in the same manner as described in Example 1, an active compound preparation which contains 0.05% of
(1a") 3-methylthio-4-amino-6-phenyl-1,2,4-triazine-5-one.

A field of dwarf beans is sprayed with this preparation of the active compound so that the dwarf beans themselves are only just dripping wet.

After 8 days the leaves are completely dried up.

The harvesting of the beans is quite considerably facilitated in this manner.

The same action is exercised by:
(29a') 3-methylthio-4-amino-6-methyl-1,2,4-triazine-5-one
(7") 3-ethylamino-4-amino-6-phenyl-1,2,4-triazine-5-one
(33') 3 methoxy-4-amino-6-phenyl-1,2,4-triazine-5-one.

The following Examples, by way of illustration and not limtation, contain detailed particulars of various methods of preparation of different 1,3,4-triazine-5-ones of the present invention. They exemplify methods which are in accordance with known types.

EXAMPLE 4

Preparation of 3-hydroxy-1,2,4-triazine-5-ones with different substituents in the 6-position:

74g carbohydrazide are heated to 90°-100° C with 600 ml water. 74g pyroracemic acid are added dropwise, with stirring. After 3 hours, filtering off cold with suction is effected to yield:
(36) 3-hydroxy-4-amino-6-methyl-1,2,4-triazine-5-one, m.p. 159° C (from alcohol).

In analogous manner there are also obtained for instance:
(37) 3-hydroxy-4-amino-6-benzyl-1,2,4-triazine-5-one, m.p. 173° C
(38) 3-hydroxy-4-amino-6-phenyl-1,2,4-triazine-5-one, m.p. 195° C

EXAMPLE 5

Modification of 3-hydroxy-1,2,4-triazine-5-ones:

20.4g 3-hydroxy-4-amino-6-phenyl-1,2,4-triazine-5-one (38') are dissolved in 300 ml dimethylformamide and 50 cc 2N sodium methylate solution. The excess methanol is then distilled off in a vacuum, and 13.5g β-diethylaminoethyl chloride are added dropwise at 80° C, with stirring, to the remaining dimethylformamide solution. After a short time the reaction mixture is neutral to phenolphthalein. The solvent is distilled off under reduced pressure. The residue is taken up in water and methylene chloride, and the organic phase is separated and fractionally distilled to yield:
(39) 3-(β-diethylaminoethoxy)-4-amino-6-phenyl-1,2,4-triazine-5-one, b.p. 160° C/0.01 mm Hg.

EXAMPLE 5A

Substitution products of 3-hydroxy-1,2,4-triazine-5-ones, indirect method of preparation:

2.3 g sodium are added to 500 ml methanol whereby a sodium methylate solution is formed. 23.4g 3-methylthio-4-amino-6-phenyl-1,2,4-triazine-5-one (1a) and 6.5 ml methyl iodide are added. The mixture is boiled for 1 hour. When cooling down the mixture, a crystalline precipitate separates. The crystals are removed by suction and recrystallized from methanol and optionally once more from acetic acid ester. The 3-methoxy-4-amino-6-phenyl-1,2,4-triazin-5one (33″) thus obtained has a melting point of 167° C.

In analogous manner to Example 5A, there are also obtained for instance:

(40) 3-methoxy-4-amino-6-methyl-1,2,4-triazine-5-one, m.p. 124° C
(41) 3-ethoxy-4-amino-6-phenyl-1,2,4-triazine-5-one, m.p. 137° C
(42) 3-butoxy-4-amino-6-phenyl-1,2,4-triazine-5-one, m.p. 77° C
(43) 3-hexoxy-4-amino-6-phenyl-1,2,4-triazine-5one, m.p. 77° C
(44) 3-allyloxy-4-amino-6-phenyl-1,2,4-triazine-5-one, m.p. 75° C
(45) 3-propargyloxy-4-amino-6-phenyl-1,2,4-triazine-5-one, m.p. 115° C
(46) 3-(3′,3′-dichlorallyloxy)-4-amino-6-phenyl-1,2,4-triazine-5-one, m.p. 84° C
(47) 3-($\beta$-diethylaminoethoxy)-4-amino-6-methyl-1,2,4-triazine-5-one, b.p. 121° C/0.01 mm Hg.
(48) 3-($\beta$-diethylaminoethoxy)-4-amino-6-benzyl-1,2,4-triazine-5-one, b.p. 165° C, 0.01 mm Hg.

EXAMPLE 6

Modification of 3-hydroxy-4-amino-1,2,4-triazine-5-ones:

10g 3-hydroxy-4-amino-6-methyl-1,2,4-triazine-5-one (36′) are boiled for 3 hours with 100 ml acetic anhydride. The excess acetic anhydride serving as solvent is distilled off in a vacuum and the residue is dissolved in, and allowed to crystallize (without filtration) from, alcohol to yield:

(49) 3-acetoxy-4-diacetylamino-6-methyl-1,2,4-triazine-5-one, m.p. 212° C.

EXAMPLE 7

Preparation of 3-mercapto-1,2,4-triazine-5-ones with different substituents in 6-position:

When 14g thiocarbohydrazide and 14g furoylformic acid are reacted according to Example 4, there is obtained

(50) 3-mercapto-4-amino-6-furyl-1,2,4-triazine-5-one, m.p. 244° C.

In analogous manner there can also be prepared for instance:

(51) 3-mercapto-4-amino-6-methyl-1,2,4-triazine-5-one, m.p. 180° C
(52) 3-mercapto-4-amino-6-benzyl-1,2,4-triazine-5-one, m.p. 205° C
(53) 3-mercapto-4-amino-6-phenyl-1,2,4-triazine-5-one, m.p. 242° C
(54) 3-mercapto-4-amino-6-isobutyl-1,2,4-triazine-5-one, m.p. 156° C
(55) 3-mercapto-4-amino-6-(4′-chlorphenyl)-1,2,4-triazine-5-one, m.p. 264° C.
(56) 3-mercapto-4-amino-6-(4′-chlorbenzyl)-1,2,4-triazine-5-one, m.p. 224° C
(57) 3-mercapto-4-amino-6-ethyl-1,2,4-triazine-5-one, m.p. 123° C
(58) 3-mercapto-4-amino-6-isopropyl-1,2,4-triazine-5-one, m.p. 140° C
(59) 3-mercapto-4-amino-6-cyclohexyl-1,2,4-triazine-5-one, m.p. 166° C
(60) 3-mercapto-4-amino-6-isopentyl-1,2,4-triazine-5-one, m.p. 143° C
(61) 3-mercapto-4-amino-6-hexyl-1,2,4-triazine-5-one, m.p. 126° C
(62) 3-mercapto-4-amino-6-carbethoxy-methyl-1,2,4-triazine-5-one, m.p. 134° C
(63) 3-mercapto-4-amino-6-(4′-methyl-phenyl)-1,2,4-triazine-5-one, m.p. 222° C
(64) 3-mercapto-4-amino-6-(3′-methyl-phenyl)-1,2,4-triazine-5-one, m.p. 214° C
(65) 3-mercapto-4-amino-6(3′-methoxy-phenyl)-1,2,4-triazine-5one, m.p. 200° C
(66) 3-mercapto-4-amino-6-(3′-chloro-phenyl)-1,2,4-triazine-5-one, m.p. 242° C
(67) 3-mercapto-4-amino-6-(4′-nitro-phenyl)-1,2,4-triazine-5one, m.p. 222° C
(68) 3-mercapto-4-amino-6-benzylmercapto-merthyl-1,2,4-triazine-5-one, m.p. 169° C
(69) 3-mercapto-4-methylamino-6-phenyl-1,2,4-triazine-5-one, m.p. 129° C
(70) 3-mercapto-4-amino-6-styryl-1,2,4-triazine-5-one, m.p. 258° C (decomp.)

EXAMPLE 8

Modification of 3-mercapto-1,2,4-triazine-5-one

When 38.7g 3-mercapto-4amino-6methyl-1,2,4-triazine-5one (51′) are reacted according to Example 5 in dimethylformamide with sodium methylate and chloride, there is obtained

(71) 3-(4-amino-6-methyl-1,2,4-triazine-5-one, b.p. 141° C/0.01 mm Hg.

In analogous manner there are also obtained for instance:

(72) 3-(4-amino-6-phenyl-1,2,4-triazine-5-one as HCl salt, m.p. 220° C
(29a 3-methylthio-4-amino-6-methyl-1,2,4-triazine-5-one, m.p. 166° C
(4″) 3-methylthio-4-amino-6benzyl-1,2,4-triazine-5-one, m.p. 205° C
(1a′3-methylthio-4-amino-6-phenyl-1,2,4-triazine-5-one, m.p. 188° C
(30′) 3-methylthio-4-amino-6-(4′-chlorbenzyl)-1,2,4-triazine-5one, m.p. 183° C
(73) 3-methylthio-4-amino-6-(4′-chlorophenyl)-1,2,4-triazine-5-one, m.p. 182° C
(5′) 3-methylthio-4-amino-6-furyl-1,2,4-triazine-5-one, m.p. 225° C
(74) 3-allylthio-4-amino-6-furyl-1,2,4-triazine-5-one, m.p. 165° C
(75) 3-propynylthio-4-amino-6-furyl-1,2,4-triazine-5-one, m.p. 174° C
(31′) 3-propynylthio-4-amino-6-phenyl-1,2,4-triazine-5-one, m.p. 159° C
(32′) 3-allylthio-4-amino-6-phenyl-1,2,4-triazine-5-one, m.p. 137° C
(76) 3-allylthio-4amino-6(4′-chlorbenzyl)-1,2,4-triazine-5one, m.p. 157° C
(77) 3-isopropylthio-4-amino-6-phenyl-1,2,4-triazine-5-one, m.p. 150° C

(78) 3-dodecylthio-4-amino-6-phenyl-1,2,4-triazine-5-one, m.p. 103° C
(79) 3-benzylthio-4-amino-6-phenyl-1,2,4-triazine-5-one, m.p. 169° C
(80) 3-(4'-chlorobenzylthio)-4-amino-6-phenyl-1,2,4-triazine-5-one, m.p. 184° C
(81) 3-(4'-chlorobenzylthio)-4-amino-6-methyl-1,2,4-triazine-5-one, m.p. 186° C
(82) 3-isobutylthio-4-amino-6-methyl-1,2,4-triazine-5-one, m.p. 65° C
(3'') 3-ethylthio-4-amino-6-phenyl-1,2,4-triazine-5-one, m.p. 114° C
(83) 3-propylthio-4-amino-6-phenyl-1,2,4-triazine-5-one, m.p. 119° C
(84) 3-butylthio-4-amino-6-phenyl-1,2,4-triazine-5-one, m.p. 100° C
(85) 3-hexylthio-4-amino-6-phenyl-1,2,4-triazine-5-one, m.p. 87° C
(86) 3-cyclohexylthio-4-amino-6-phenyl-1,2,4-triazine-5-one, m.p. 160° C
(87) 3-(2,3-dichlorallythio)-4-amino-6-phenyl-1,2,4-triazine-5-one, m.p. 215° C
(88) 3-octadecylthio-4-amino-6-phenyl-1,2,4-triazine-5-one, m.p. 94° C
(22'') 3-methylthio-4-amino-6-ethyl-1,2,4-triazine-5-one, m.p. 120° C
(21') 3-methylthio-4-amino-6-isopropyl-1,2,4-triazine-5-one, m.p. 123° C
(2'') 3-methylthio-4-amino-6-cyclohexyl-1,2,4-triazine-5-one, m.p. 154° C
(11'') 3-methylthio-4-amino-6-isobutyl-1,2,4-triazine-5-one, m.p. 66° C
(23'') 3-methylthio-4-amino-6-isopentyl-1,2,4-triazine-5-one, stiff oil
(24'') 3-methylthio-4-amino-6-n-hexyl-1,2,4-triazine-5-one, m.p. 63° C
(89) 3-methylthio-4-amino-6-styryl-1,2,4-triazine-5-one, m.p. 218° C
(90) 3-methylthio-4-amino-6-carbomethoxy-methyl-1,2,4-triazine-5-one, m.p. 112° C
(91) 3-methylthio-4-amino-6-(3'-methyl-phenyl)-1,2,4-triazine-5-one, m.p. 160° C
(92) 3-methylthio-4-amino-6-(4'-methyl-phenyl)-1,2,4-triazine-5-one, m.p. 185° C
(93) 3-methylthio-4-amino-6-(3'-chloro-phenyl)-1,2,4-triazine-5-one, m.p. 219° C
(94) 3-methylthio-4-amino-6-(3'-methoxy-phenyl)-1,2,4-triazine-5-one, m.p. 142° C
(95) 3-methylthio-4-amino-6-benzylmercapto-methyl-1,2,4-triazine-5-one, m.p. 110° C

EXAMPLE 9

Modification of 3-methylthio-1,2,4-triazine-5-ones:

11.7g 3-methylthio-4-amino-6-methyl-1,2,4-triazine-5-one (29a'and 15g p-chloraniline are stirred together with each other for 1 hour at 150° C and then 1 hour at 160° C. After this the melt has become solid. After cooling, the melt is boiled out with ether. The insoluble portion is dissolved in, and allowed to crystallize (without filtration) from, dimethylformamide. There is obtained

(96) 3-(4'-chlorophenylamino)-4-amino-6-methyl-1,2,4-triazine-5-one, m.p. 242° C:

When, instead of p-chloraniline, an amine is used with which, because of its volatility, the above-mentioned reaction temperatures cannot be achieved in an open vessel, the work is carried out in an autoclave.

The following compounds for instance can also be prepared in this manner:

(97) 3-(3',4'-dichlorphenylamino)-4-amino-6-methyl-1,2,4-triazine-5-one, m.p. 228° C
(98) 3-(2',4'-dichlorphenylamino)-4-amino-6-methyl-1,2,4-triazine-5-one, m.p. 218° C
(99) 3-(β-diethylaminoethylamino)-4-amino-6-methyl-1,2,4-triazine-5-one, m.p. 108° C
(34') 3-methylamino-4-amino-6-amino-6-methyl-1,2,4-triazine-5-one, m.p. 180° C
(7''') 3-ethylamino-4-amino-6-phenyl-1,2,4-triazine-5-one, m.p. 158° C
(9'') 3-methylamino-4-amino-6-phenyl-1,2,4-triazine-5-one, m.p. 212° C
(100a) 3-n-butylamino-4-amino-6-phenyl-1,2,4-triazine-5-one, m.p. 182° C
(12') 3-n-propylamino-4-amino-6-phenyl-1,2,4-triazine-5-one, m.p. 176° C
(13a'') 3-morpholino-4-amino-6-phenyl-1,2,4-triazine-5-one, m.p. 163° C
(101) 3-(β-diethylaminoethylamino)-4-amino-6-phenyl-1,2,4-triazine-5-one, m.p. 130° C
(102a) 3-benzylamino-4-amino-6-phenyl-1,2,4-triazine-5-one, m.p. 177° C
(103) 3-(4'-chloranilino)-4-amino-6-phenyl-1,2,4-triazine-5-one, m.p. 257° C
(104) 3-(4'-chloranilino)-4-amino-6-(4'-chlorobenzyl)-1,2,4-triazine-5-one, m.p. 212° C
(105) 3-(β-diethylaminoethylamino)-4-amino-6-(4'-chloro benzyl)-1,2,4-triazine-5-one, m.p. 148° C
(10'') 3-methylamino-4-amino-6-(4'-chlorbenzyl)-1,2,4-triazine-5-one, m.p. 159° C
(106) 3-benzylamino-4-amino-6-(4'-chlorbenzyl)-1,2,4-triazine-5-one, m.p. 123° C
(107) 3-(β-diethylaminoethylamino)-4-amino-6-(4'-chlorphenyl)-1,2,4-triazine-5-one, m.p. 184° C
(25') 3-piperidino-4-amino-6-phenyl-1,2,4-tirazine-5-one, m.p. 149° C
(26'') 3-allylamino-4-amino-6-phenyl-1,2,4-triazine-5-one, m.p. 168° C
(108) 3-octadecylamino-4-amino-6-phenyl-1,2,4-triazine-5-one, m.p. 129° C
(109) 3-n-hexylamino-4-amino-6-phenyl-1,2,4-triazine-5-one, m.p. 164° C
(110) 3-[2'-(ethyl)-hexylamino]-4-amino-6-phenyl-1,2,4-triazine-5-one, m.p. 131° C
(16'') 3-dimethylamino-4-amino-6-phenyl-1,2,4-triazine-5-one, m.p. 133° C

EXAMPLE 10

Preparation of 3,4-diamino-1,2,4-triazine-5-ones:

43g 1,3-diamino-guanidine-hydrobromide are dissolved in a little water; 38g benzoylformic acid, dissolved in methanol, are added. After brief heating, cooling is effected followed by neutralization with bicarbonate. There is obtained in this way (112a) 3,4-diamino-6-phenyl-1,2,4-triazine-5-one, m.p. 258° C.

In analogous manner, with p-chlorbenzoylformic acid there is prepared (113) 3,4-diamino-6-(4'-chlorphenyl)-1,2,4-triazine-5-one, m.p. 255° C.

EXAMPLE 11

Preparation of 3-methylthio-4-acetylamino-6-phenyl-1,2,4-triazine-5-one:

20g 3-methylthio-4-amino-6-phenyl-1,2,4-triazine-5-one (1a''''') are boiled for 9 hours with 100 cc acetic anhydride. The excess anhydride is then distilled off under reduced pressure. The crystalline residue is dissovled in, and allowed to crystallize (without filtration) from, alcohol to yield:

(6') 3-methylthio-4-diacetylamino-6-phenyl-1,2,4-triazine-5-one, m.p. 122° C 20g of this last mentioned compound are dissolved in alcohol and treated at 20° C with an equivalent of 2N sodium hydroxide solution, which is consumed very rapidly. After working up, there is obtained (8') 3-methylthio-4-acetylamino-6-phenyl-1,2,4-triazine-5-one, m.p. 213° C.

EXAMPLE 12

Modification of 3-methylthio-4-amino-1,2,4-triazine-5-one at the amino group:

23.4g 3-methylthio-4amino-6-phenyl-1,2,4-triazine-5-one (1a''''') are dissolved in 100 ml chlorobenzene with 17.8g freshly distilled chloral and 0.2g p-toluenesulfonic acid. The reaction mixture is heated for 1 hour on a water-bath and then for 45 minutes under reflux. A small amount of undissolved mater is filtered off hot. From the filtrate there crystallizes (20'') 3-methylthio-4-($\beta$-trichloro-$\alpha$-hydroxy-ethyl)-amino-6-phenyl-1,2,4-triazine-5-one.

After dissolving in, and allowing to crystallize (without filtation) from, chloroform, such product has: m.p. 147° C (decomp.).

EXAMPLE 12A

Modification of 3-methylthio-4-amino-1,2,4-triazine-5-ones by -ylidene substitution at the 4-position amino group:

11.7g 3-methylthio-4-amino-6-phenyl-1,2,4-triazine-5-one (1a'''''') and 5.6g cyclohexanone are boiled for 1 hour in 50 ml methanol after the addition of 5 drops of concentrated hydrochloric acid. The crystals which have precipitated during cooling are dissolved in, and allowed to recrystallized (without filtation) from, methanol to yield:

(18'') 3-methylthio-4-cyclohexylidene-amino-6-phenyl-1,2,4-triazine-5-one, m.p. 140° C.

In analogous manner, there are also obtained for instance:

(15'') 3-methylthio-4-benzylidene-amino-6-phenyl-1,2,4-triazine-5-one m.p. 180° C (14'') 3-methylthio-4-(furfur-2'-ylidene-amino)-6-phenyl-1,2,4-triazine-5-one, m.p. 172° C (35') 3-methylthio-4-(5'-nitro-furfur-2'-ylidene-amino)-6-phenyl-1,2,4-triazine-5-one, m.p. 207° C (17'') 3-methylthio-4-(prop-2'-ylidene-amino)-6-phenyl-1,2,4-triazine-5-one, m.p. 152° C (19'') 3-methylthio-4-(isobutylidene-amino)-6-phenyl-1,2,4-triazine-5-one, m.p. 136° C (27'') 3-methylthio-4-(1'-phenyl-eth-1'-ylidene-amino)-6-phenyl-1,2,4-triazine-5-one, m.p. 154° C (28'') 3-methylthio-4-(pyrid-2'-yl-methylidene-amino)-6-phenyl-1,2,4-triazine-5-one, m.p. 205° C

EXAMPLE 13

In the same manner as described in Example 4, using corresponding molar amounts of the appropriate starting materials, the following compounds are produced:

(114) 3-naphth-1'-yl-n-propyloxy-4-isooctylamino-6-hexadec-1''-yl-1,2,4-triazine-5-one (115) 3-phenyl-tert-butyloxy-4-formylamino-6-vinyl-1,2,4-triazine-5-one (116) 3-naphth-1'-yloxy-4-butanoylamino-6-dodec-11''-en-1''-yl-1,2,4-triazine-5-one (117) 3-cyclopent-3'-enyloxy-4-(2''-cyano-prop-1''-yl-amino)-6-prop-2'''-yn-1'''-yl-1,2,4-triazine-5-one (118) 3-(3'-nitro-4'-bromo-5'-fluoro-hept-6'-yn-1'-yloxy)-4-($\alpha$-bromo-$\alpha$-fluoro-acetylamino)-6-octadec-9''-yn-1''-yl-1,2,4-triazine-5-one (119) 3-(3'-iodo-5'-fluoro-cyclohexyloxy)-4-hex-1''-ylidene-amino-6-naphth-1'''-ylmethyl-1,2,4-triazine-5-one (120) 3-[$\beta$-(3'-methoxy-4'-sec-butyl-5'-chloro-phenyl) ethyloxy]-4-cyclopentylidene-amino-6-naphth-1''-ylisopropyl-1,2,4-triazine-5-one (121) 3-(4'-phenoxynaphth-1'-yloxy-4- (3''-phenyl-n-prop-1''-ylidene-amino)-6-naphth-1'''-yl-n-but-2''''-en-1''''-yl-1,2,4-triazine-5-one (122) 3-($\beta$-naphth-1'-ylethylmercapto)-4-[5''-(3'''-chloro-4'''-bromo-5'''-iodo-phenyl) pent-1''-ylidene-amino]-6-naphth-1''''-yl-1,2,4-triazine-5-one (123) 3-phenyl-isopropylmercapto-4-[2'-(4''-n-butoxyphenyl) eth-1'-ylidene-amino]-6-($\alpha$-tetrahydrofuryl)-1,2,4-triazine-5-one (124) 3-naphth-1'-ylmercapto-4-[4''-(4'''-nitronaphth-1'''-yl)cyclohex-1''-ylidene-amino]-6-piperid-1''0'''-yl-1,2,4-triazine-5-one (125) 3-cyclohex-3'-enylmercapto-4-piperid-1''-yl-6-morpholino-1,2,4-triazine-5-one (126) 3-(5'-chloro-5'-bromo-10'-nitro-dec-9'-yl-mercapto)-4-o-thiazolidin-2''-yl-6-thianyl-1,2,4-triazine-5-one (127) 3-[3''-ethoxy-5''-isopropyl-naphth-1''-yl)-prop-1'-ylmercapto]-4-(3'''-$\Delta^{2,5}$-pyran-2''''-yl-cyclopent-1'''-ylidene-amino)-6-(10''''bromodec-1''''''-yl)-1,2,4-triazine -5-one (128) 3-(3'-naphth-1'-yloxy-phenylmercapto)-4-pyrazol-1''-yl-6-(3'''-iodo-4'''-fluoro-cyclopent-2'''-enyl)-1,2,4-triazine-5-one (129) 3-($\beta$-phenyl-ethylamino)-4-(1',2',3'-dioxazol-3'-yl)-6-(3''-isopropylmercaptoallyl)-1,2,4-triazine-5-one (130) 3-[N-(2'-nitro-3'-iodo-4'-chloro-5'-ethyl-phenyl)-N-cyclohexyl-amino]-4-(1'', 2''-dyhydro-pyrimidin-1'-yl)-6-(4'''-phenyloxy pyrid-2'''-yl)-1,2,4-triazine-5-one (131) 3-[N-(3'-n-propoxy-4'-phenyloxy-cyclohexyl)-N-isohexyl-amino]-4-pyrrol-1''-yl-6-(4'''-phenylmercapto-but-3'''-yn-1'''-yl)-1,2,4-triazine-5-one (132) 3-(4'-naphth-1''-yloxy phenyl-amino)-4-(1''',2''',5'''-pyrrodiazol-1'''-yl)-6-(3''''-naphth-1'''''-ylmercapto-4''''-carbomethoxy-$\alpha$-furyl)-1,2,4-triazone-5-one (133) 3-(metathiazolidino)-4-(1',2',3'-thiodiazolidin-2'-yl)-6-[3''-(3'''-chloro-4'''-nitro-5'''-ethoxy-phenyl)-prop-1''-yl]-1,2,4-triazine-5-one

EXAMPLE 14

Preparation of 3-hydroxy-1,2,4-triazine-5-ones with different substituents at the 6-position:

In analogous manner to the procedure of Example 4, the following compounds are also obtained:
(134) 3-hydroxy-4-amino-6-tert.-butyl-1,2,4-triazine-5-one, w.p. 166° C
(135) 3-hydroxy-4-amino-6-isopropyl-1,2,4-triazine-5-one, m.p. 124° C

EXAMPLE 15

Modification of 3-hydroxy-1,2,4-triazine-5-ones:
In analogous manner to the procedure of Example 5A, the following compounds are also obtained:
(136) 3-methoxy-4-amino-6-isopropyl-1,2,4-triazine-5-one, m.p. 114° C
(137) 3-methoxy-4-amino-6-tert.-butyl-1,2,4-triazine-5-one, m.p. 173° C
(138) 3-methoxy-4-amino-6-cyclohexyl-1,2,4-triazine-5-one, m.p. 131° C

EXAMPLE 16

Modification of 3-methoxy-4-amino-1,2,4-triazine-5-one at the 4-position amino group (analogous to Example 12):

9.9g 3-methoxy-4-amino-6-isopropyl-1,2,4-triazine-5-one (136) are dissolved at 40° C with stirring in 50 ml anhydrous chloroform and then reacted with 7.4g freshly distilled chloral and 0.2g of trichloroacetic acid. After subsidance of the exothermic reaction, crystallization is completed by adding 150 ml of petroleum ether. In this manner, there is obtained:
(139) 3-methoxy-4-(β-trichloro-α-hydroxy-ethyl)-amino-6-isopropyl-1,2,4-triazine-5-one, m.p. 165° C

EXAMPLE 17

Preparation of 3-mercapto-1,2,4-triazine-5-ones with different substituents at the 6-position:
In analogous manner to the procedure of Example 7, the following compounds are also obtained:
(140) 3-mercapto-4-amino-6-tert.-butyl-1,2,4-triazine-5-one, m.p. 214° C
(141) 3-mercapto-4-amino-6-n-propyl-1,2,4-triazine-5-one, m.p. 128° C
(142) 3-mercapto-4-amino-6-(adamant-2'-yl)-1,2,4-triazine-5-one, m.p. 279° C (decomp.)
(143) 3-mercapto-4-amino-6tetrahydropyran-2'-yl-α,2,4,triazine-5-one, m.p. 152° C
(144) 3-mercapto-4-amino-6-(furfur-2'-yl)-1,2,4-triazine-5-one, m.p. 152° C
(145) 3-mercapto-4-amino-6-(pyrid-2'-yl-methyl)-1,2,4-triazine-5-one, m.p. 240° C (decomp)
(146) 3-mercapto-4-amino-6-(pyrid-4'-yl-methyl)-1,2,4-triazine-5-one, m.p. 215° C (decomp.)

EXAMPLE 18

Modification of 3-mercapto-1,2,4-triazine-5-ones:
In analogous manner to the procedure of Example 8, the following compounds are also obtained:
(147) 3-methylthio-4-amino-6-tert.-butyl-1,2,4-triazine-5-one, m.p. 127° C
(148) 3-ethylthio-41 -amino-6-isopropyl-1,2,4-triazine-5-one, m.p. 115° C
(149) 3-n-butylthio-4-amino-6 -isopropyl-1,2,4-triazine-5-one, m.p. 78° C
(150) 3-(α-allylthio)-4-amino-6-isopropyl-1,2,4-triazine-5-one, m.p. 81° C
(151) 3-isopropylthio-4-amino-6-methyl-1,2,4-triazine-5-one, m.p. 149° C
(152) 3-isopropylthio-4-amino-6-isopropyl-1,2,4-triazine-5-one, m.p. 70° C
(153) 3-methylthio-4-amino-6-n-propyl-1,2,4-triazine-5-one, m.p. 81° C
(154) 3-methylthio-4-amino-6-adamant-2'-yl-1,2,4-triazine-5-one, m.p. 235° C (decomp.)
(155) 3-ethylthio-4-amino-6-tert.-butyl-1,2,4-triazine-5-one, m.p. 82° C
(156) 3-(α-allylthio)-4-amino-6-tert.-butyl-1,2,4-triazine-5-one, m.p. 91° C
(157) 3-(β-n-butylthio-ethylthio)-4-amino-6-isopropyl-1,2,4-triazine-5-one, m.p. 56° C
(158) 3-propargylthio-4-amino-6-isopropyl-1,2,4-triazine-5-one, m.p. 103° C
(159) 3-(4'-chloro-phenylthiomethylthio)-4-amino-6-isopropyl-1,2,4-triazine-5-one, m.p. 116° C
(160) 3-(β-ethylthio-ethylthio)-4-amino-6-isopropyl-1,2,4-triazine-5-one, m.p. 87° C
(161) 3-(β-ethylthio-ethylthio)-4-amino-6-cyclohexyl-1,2,4-triazine-5-one, m.p. 77° C
(162) 3-(β-ethylthio-ethylthio)-4-amino-6-tert.-butyl-1,2,4-triazine-5-one, m.p. 53° C
(163) 3-methylthio-4-amino-6-(tetrahydropyran-2'-yl)-1,2,4-triazine-5-one, m.p. 180° C
(164) 3-methylthio-4-dimethylamino-6-isopropyl-1,2,4-triazine-5-one, m.p. 64° C
(165) 3-benzylthio-4-amino-6-isopropyl-1,2,4-triazine-5-one, m.p. 153° C
(166) 3-methylthio-4-dimethylamino-6-tert.-butyl-1,2,4-triazine-5-one, m.p. 98° C
(167) 3-methylthio-4-amino-6-(furfur-2'-yl)-1,2,4-triazine-5one, m.p. 124° C

EXAMPLE 19

Modification of 3-methylthio-1,2,4-triazine-5-ones:
In analogous manner to the procedure of Example 9, following compounds are also obtained:
(168) 3-morpholino-4-amino-6-isopropyl-1,2,4-triazine-5-one, m.p. 139° C
(169) 3-n-butylamino-4-amino-6-isopropyl-1,2,4-triazine-5-one, m.p. 125° C
(170) 3-benzylamino-4-amino-6-isopropyl-1,2,4-triazine-5-one, m.p. 144° C
(171) 3-anilino-4-amino-6-isopropyl-1,2,4-triazine-5-one, m.p. 162° C
(172) 3-methylamino-4-amino-6-isopropyl-1,2,4-triazine-5-one, m.p. 141° C
(173) 3-(2'-chloro-benzylamino)-4-amino-6-isopropyl-1,2,4-triazine-5-one, m.p. 162° C
(174) 3-(3'-chloro-benzylamino)-4-amino-6-isopropyl-1,2,4-triazine-5-one, m.p. 156° C
(175) 3-methylamino-4-amino-6-tert.-butyl-1,2,4-triazine-5-one, m.p. 219° C
(176) 3-ethylamino-4-amino-6-tert.-butyl-1,2,4-triazine-5-one, m.p. 178° C
(177) 3-ethylamino-4-amino-6-isopropyl-1,2,4-triazine-5-one, m.p. 158° C
(178) 3-n-propylamino-4-amino-6-isopropyl-1,2,4-triazine-5-one, m.p. 155° C
(179) 3-(α-allylamino)-4-amino-6-isopropyl-1,2,4-triazine-5-one, m.p. 147° C
(180) 3-dimethylamino-4-amino-6-isopropyl-1,2,4-triazine-5-one, m.p. 52° C
(181) 3-n-dodecylamino-4-amino-6-isopropyl-1,2,4-triazine-5-one, m.p. 104° C
(182) 3-n-butylamino-4-amino-6-cyclohexyl-1,2,4-triazine-5-one, m.p. 173° C
(183) 3-(4'-chloro-anilino)-4-amino-6-isopropyl-1,2,4-triazine-5-one, m.p. 232° C (184) 3-(3',4'-dichloro-anilino)-4-amino-6-isopropyl-1,2,4-triazine-5-one, m.p. 192° C
(185) 3-isopropylamino-4-amino-6-isopropyl-1,2,4-triazine-5-one, m.p. 173° C
(186) 3-isobutylamino-4l-amino-6-isopropyl-1,2,4-triazine-5-one, m.p. 73° C
(187) 3-dimethylamino-4-amino-6-tert.-butyl-1,2,4-triazine-5-one, m.p. 86° C
(188) 3-dimethylamino-4-amino-6-cyclohexyl-1,2,4-triazine5-one, m.p. 129° C
(189) 3-methylamino-4-amino-6-cyclohexyl-1,2,4-triazine-5-one, m.p. 141° C

EXAMPLE 20

Preparation of 3,4-diamino-1,2,4-triazine-5-one:
On analogous manner to the procedure of Example 10, the following compound is also obtained:
(190) 3,4-diamino-6-tert.-butyl-1,2,4-triazine-5-one, m.p. 232° C (decomp.)

EXAMPLE 21

Modification of 3-methylthio-4-amino-1,2,4-triazine-5-ones at the 4-position amino group:
In analogous manner to the procedure of Example 12, the following compounds are also obtained:
(191) 3-methylthio-4-(β-trichroro-α-hydroxy-ethyl)-amino-6-isopropyl-1,2,4-triazine-5-one, m.p. 123° C
(192) 3-methylthio-4-(β-trichloro-6a-hydroxy-ethyl)-amino-6-tort.-butyl-1,2,4-triazine-5-one, m.p. 166° C
(193) 3-methylthio-4-(β-trichloro-α-hydroxy-ethyl)-amino-6-cyclohexyl-1,2,4-triazine-5-one, m.p. 157° C

EXAMPLE 22

Modification of 3-methylthio-4-amino-1,2,4-triazine-5-ones by -ylidene substitution at the 4-position amino group:
In analogous manner to the procedure to Example 12A, the following compounds are also obtained:
(194) 3-methylthio-4-(prop-2'-ylidene-amino)-6-isopropyl-1,2,4-triazine-5-one, m.p. 50° C
(195) 3-methylthio-4-(3'-methyl-but-2'-ylidene-amino)-6-phenyl-1,2,4-triazine-5-one, m.p. 84° C
(196) 3-methylthio-4-(3',3'-dimethyl-but-2'ylidene-amino)-6-phenyl-1,2,4-triazine-5-one, m.p. 102° C
(197) 3-methylthio-4-(hexahydrobenzylidene-amino)-6-isopropyl-1,2,4-triazine-5-one, m.p. 63° C
(198) 3-methylthio-4-(benzylidene-amino)-6-isopropyl-1,2,4-triazine-5-one, m.p. 150° C
(199) 3-methylthio-4-(2'-chloro-benzylidene-amino)-6-isopropyl-1,2,4-triazine-5-one, m.p. 196° C
(200) 3-methlthio-4-(3'-chlorobenzylidene-amino)-6-isopropyl-1,2,4-triazine-5-one, m.p. 139° C
(201) 3-methylthio-4-(4'-chloro-benzylidene-amino)-6-isopropyl-1,2,4-triazine-5-one, m.p. 140° C
(202) 3-methylthio-4-(2',6'-dichloro-benzylidene-amino)-6-isopropyl-1,2,4-triazine-5-one, m.p. 177° C
(203) 3-methylthio-4-(furfur-2'-ylidene-amino)-6-isopropyl-1,2,4-triazine-5one, m.p. 143° C
(204) 3-methylthio-4-(cyclohexylidene-amino)-6-isopropyl-1,2,4-triazine-5-one, m.p. 86° C
(205) 3-methylthio-4-(1'-phenyleth-1'-ylidene-amino)-6-isopropyl-1,2,4-triazine-5-one, m.p. 116° C
(206) 3-methylthio-4-(2'-methyl-benzylidene-amino)-6-isopropyl-1,2,4-triazine-5-one, m.p. 137° C
(207) 3-metylthio-4-(4'-methoxy-benzylidene-amino)-6-isopropyl-1,2,4-triazine-5-one, m.p. 105° C
(208) 3-methylthio-4-(2',4'-dichloro-benzylidene-amino)-6-isopropyl-1,2,4-triazine-5-one, m.p. 124° C
(209) 3-methylthio-4-(340-nitro-benzylidene-amino)-6-isopropyl-1,2,4-triazine-5-one, m.p. 187° C
(210) 3-methylthio-4-(4'-nitro-benzylidene-amino)-6-isopropyl-1,2,4-triazine-5-one, m.p. 116° C
(211) 3-methylthio-4-(2'-chloro-5'-nitro-benzylidene-amino)-6-isopropyl-1,2,4-triazine-5-one, m.p. 241° C
(212) 3-methylthio-4-(cinnamylidene-amino)-6-isopropyl-1,2,4-triazine-5-one, m.p. 139° C
(213) 3-methylthio-4-(4'-methyl-benzylidene-amino)-6-isopropyl-1,2,4-triazine-5-one, m.p. 100° C
(214) 3-methylthio-4-(isobutylidene-amino)-6-isopropyl-1,2,4-triazine-5-one, m.p. 55° C
(215) 3-methylthio-4-(isobutylidene-amino)-6-tert.-butyl-1,2,4-triazine-5-one, m.p. 156° C
(216) 3-metylthio-4-(n-propylidene-amino)-6-isopropyl-1,2,4-triazine-5-one, m.p. 82° C
(217) 3-methylthio-4-(n-butylidene-amino)-6-isopropyl-1,2,4-triazine-5-one, m.p. 37° C
(218) 3-methylthio-4-(3'-phenyl-prop-1'-ylidene-amino)-6-isopropyl-1,2,4-triazine-5-one, m.p. 111° C
(219) 3-methylthio-4-(2'-ethyl-hex-1'-ylidene-amino)-6-isopropyl-1,2,4-triazine-5-one (oil)
(220) 3-methylthio-4-(prop-2'-ylidene-amino)-6-tert.-butyl-1,2,4-triazine-5-one, m.p. 129° C
(221) 3-methylthio-4-(cyclohexylidene-amino)-6-tert.-butyl-1,2,4-triazine-5-one, m.p. 121° C
(222) 3-methylthio-4-(furfur-2'-ylidene-amino)-6-tert.-butyl-1,2,4-triazine-5-one, m.p. 162° C
(223) 3-methylthio-4-(cyclopentylidene-amino)-6-isopropyl-1,2,4-triazine-5-one, m.p. 78° C
(224) 3-methylthio-4-(prop-2'-ylidene-amino)-6-cyclohexyl-1,2,4-triazine-5-one, m.p. 131° C
(225) 3-methylthio-4-(benzylidene-amino)-6-cyclohexyl-1,2,4-triazine-5-one, m.p. 124° C
(226) 3-methylthio-4-(furfur-2'-ylidene-amino)-6-cyclohexyl-1,2,4-triazine-5-one, m.p. 113° C
(227) 3-methylthio-4-(cyclohexylidene-amino)-6-cyclohexyl-1,2,4-triazine-5-one, m.p. 94° C
(228) 3-methylthio-4-(hexahydrobenzylidene-amino)-6-cyclohexyl-1,2,4-triazine-5-one, m.p. 62° C
(229) 3-methylthio-4-(isobutylidene-amino)-6-cyclohexyl-1,2,4-triazine-5-one (viscous oil)

EXAMPLE 23

Modification of 3-methylthio-4-amino-1,2,4-triazine-5-ones by -ylidene substitution at the 4-position amino group (analogous to Examples 12A and 22):
19.7g of 3-methylamino-4-amino-6-tert.-butyl-1,2,4-triazine-5-one (175) are reacted in 100 ml of isopropanol with 10.6g of benzaldehyde and 10 ml of concentrated hydrochloric acid. Stirring is effected for several hours at 30° C, until the resulting precipitation of the corresponding hydrochloride salt ceases. The hydrochloride salt is separated by suction filtration, dissolved in 50 ml of ethanol, and the ethanol solution rendered alkaline by the addition of 10 ml of concentrated aqueous ammonia whereby the following compound crystallizes out:
(230) 3-methylamino-4-(benzylidene-amino)-6-tert.-butyl-1,2,4-triazine-5-one, m.p. 146° C
In analogous manner, the following compounds are also obtained:

(231) 3-methylamino-4-(furfur-2'-ylidene-amino)-6-tert.-butyl-1,2,4-triazine-5-one, m.p. 142° C
(232) 3-methylamino-4-(prop-2'-ylidene-amisno)-6-tert.-butyl-1,2,4triazine-5-one, m.p. 189° C
(233) 3-methylamino-4-(4'-chloro-benzylidene-amino)-6-tert.-butyl-1,2,4-triazine-5-one, m.p. 147° C

EXAMPLE 24

Modification of 3-hydroxy-1,2,4-triazine-5-one:

In analogous manner to the procedure of Example 5A, the following compound is also obtained:
(234) 3-methoxy-4-methylamino-6-phenyl-1,2,4-triazine-5-one.

EXAMPLE 25

The procedure of Example 1 is repeated, and the particular active compounds tested, the amounts applied, and the results obtained can be seen from the following Table 1D:

TABLE 1D

| Active compound | Pre-emergence test Active compound used in Kg/hectare | Oats | Wheat | Cotton | Sinapis | Cheno-podium | Echino-chloa |
|---|---|---|---|---|---|---|---|
| (1a) | 5 | 5 | 5 | 3 | 5 | 5 | 5 |
|  | 2.5 | 5 | 5 | 1 | 5 | 5 | 5 |
|  | 1.25 | 3 | 2 | 0 | 5 | 5 | 4–5 |
| (29a) | 5 | 1 | 2 | 0 | 4 | 3 | 1 |
|  | 2.5 | 1 | 0 | 0 | 3 | 2 | 0 |
|  | 1.25 | 0 | 0 | 0 | 1 | 1 | 0 |
| (22) | 5 | 5 | 4–5 | 5 | 5 | 5 | 5 |
|  | 2.5 | 5 | 4 | 4 | 5 | 5 | 5 |
|  | 1.25 | 4 | 3 | 3 | 5 | 5 | 5 |
| *(21) | 5 | 5 | 5 | 5 | 5 | 5 | 5 |
|  | 2.5 | 5 | 5 | 5 | 5 | 5 | 5 |
|  | 1.25 | 5 | 5 | 5 | 5 | 5 | 5 |
| *(147) | 5 | 5 | 5 | 5 | 5 | 5 | 5 |
|  | 2.5 | 5 | 5 | 5 | 5 | 5 | 5 |
|  | 1.25 | 5 | 5 | 5 | 5 | 5 | 5 |
| *(11) | 5 | 5 | 5 | 5 | 5 | 5 | 5 |
|  | 2.5 | 5 | 5 | 5 | 5 | 5 | 5 |
|  | 1.25 | 5 | 5 | 5 | 5 | 5 | 5 |

TABLE 1D-continued

| Active compound | Pre-emergence test Active compound used in Kg/hectare | Oats | Wheat | Cotton | Sinapis | Cheno-podium | Echino-chloa |
|---|---|---|---|---|---|---|---|
| *(23) [CH₃-CH(CH₃)-CH₂-CH₂- substituted triazinone with N-NH₂ and C-S-CH₃] | 5<br>2.5<br>1.25 | 5<br>5<br>5 | 5<br>5<br>5 | 5<br>5<br>5 | 5<br>5<br>5 | 5<br>5<br>5 | 5<br>5<br>5 |
| (148) [isopropyl triazinone with N-NH₂ and C-S-C₂H₅] | 5<br>2.5<br>1.25 | 4-5<br>4-5<br>4-5 | 4<br>4<br>3-4 | 4-5<br>4-5<br>4 | 5<br>5<br>5 | 5<br>5<br>5 | 5<br>5<br>5 |
| (153) [n-C₃H₇ triazinone with N-NH₂ and C-S-CH₃] | 5<br>2.5<br>1.25 | 5<br>4-5<br>4-5 | 4<br>4<br>3 | 5<br>5<br>4-5 | 5<br>5<br>5 | 5<br>5<br>5 | 5<br>5<br>5 |
| *(158) [isopropyl triazinone with N-NH₂ and C-S-CH₂-C≡CH] | 5<br>2.5<br>1.25 | 5<br>5<br>5 | 5<br>5<br>4 | 5<br>5<br>4 | 5<br>5<br>5 | 5<br>5<br>5 | 5<br>5<br>5 |
| *(163) [dihydropyran substituted triazinone with N-NH₂ and C-S-CH₃] | 5<br>2.5<br>1.25 | 5<br>5<br>5 | 5<br>5<br>5 | 5<br>5<br>5 | 5<br>5<br>5 | 5<br>5<br>5 | 5<br>5<br>5 |
| *(214) [isopropyl triazinone with N-N=CH-CH(CH₃)₂ and C-S-CH₃] | 5<br>2.5<br>1.25 | 5<br>5<br>5 | 5<br>4-5<br>4 | 5<br>5<br>5 | 5<br>5<br>5 | 5<br>5<br>5 | 5<br>5<br>5 |
| *(197) [isopropyl triazinone with N-N=CH-cyclohexyl and C-S-CH₃] | 5<br>2.5<br>1.25 | 5<br>5<br>5 | 5<br>5<br>4-5 | 5<br>5<br>5 | 5<br>5<br>5 | 5<br>5<br>5 | 5<br>5<br>5 |
| *(198) [isopropyl triazinone with N-N=CH-phenyl and C-S-CH₃] | 5<br>2.5<br>1.25 | 5<br>5<br>5 | 5<br>5<br>4-5 | 5<br>5<br>5 | 5<br>5<br>5 | 5<br>5<br>5 | 5<br>5<br>5 |

TABLE 1D-continued

| Active compound | | Pre-emergence test Active compound used in Kg/hectare | Oats | Wheat | Cotton | Sinapis | Cheno-podium | Echino-chloa |
|---|---|---|---|---|---|---|---|---|
| *(206) | [structure: 6-isopropyl-3-methylthio-4-(2-methylbenzylidene-amino)-1,2,4-triazin-5(4H)-one] | 5<br>2.5<br>1.25 | 5<br>5<br>5 | 5<br>5<br>5 | 5<br>5<br>4–5 | 5<br>5<br>5 | 5<br>5<br>5 | 5<br>5<br>5 |
| (213) | [structure: 6-isopropyl-3-methylthio-4-(4-methylbenzylidene-amino)-1,2,4-triazin-5(4H)-one] | 5<br>2.5<br>1.25 | 5<br>4–5<br>4–5 | 4<br>4<br>3 | 4–5<br>4–5<br>4 | 5<br>5<br>5 | 5<br>5<br>5 | 5<br>5<br>4–5 |
| (207) | [structure: 6-isopropyl-3-methylthio-4-(4-methoxybenzylidene-amino)-1,2,4-triazin-5(4H)-one] | 5<br>2.5<br>1.25 | 4–5<br>4<br>4 | 4–5<br>4<br>4 | 4–5<br>4<br>4 | 5<br>5<br>5 | 5<br>5<br>5 | 5<br>5<br>5 |
| *(201) | [structure: 6-isopropyl-3-methylthio-4-(4-chlorobenzylidene-amino)-1,2,4-triazin-5(4H)-one] | 5<br>2.5<br>1.25 | 5<br>5<br>5 | 5<br>5<br>4–5 | 5<br>5<br>5 | 5<br>5<br>5 | 5<br>5<br>5 | 5<br>5<br>5 |
| (209) | [structure: 6-isopropyl-3-methylthio-4-(3-nitrobenzylidene-amino)-1,2,4-triazin-5(4H)-one] | 5<br>2.5<br>1.25 | 4–5<br>4–5<br>4 | 4<br>4<br>3 | 4–5<br>4–5<br>4–5 | 5<br>5<br>4 | 5<br>4–5<br>4–5 | 5<br>5<br>4 |
| (210) | [structure: 6-isopropyl-3-methylthio-4-(4-nitrobenzylidene-amino)-1,2,4-triazin-5(4H)-one] | 5<br>2.5<br>1.25 | 4–5<br>4–5<br>3 | 4<br>4<br>3 | 4–5<br>4–5<br>3 | 5<br>5<br>5 | 5<br>5<br>4 | 5<br>5<br>4 |
| *(203) | [structure: 6-isopropyl-3-methylthio-4-(furfurylidene-amino)-1,2,4-triazin-5(4H)-one] | 5<br>2.5<br>1.25 | 5<br>5<br>5 | 5<br>5<br>4 | 5<br>5<br>4–5 | 5<br>5<br>5 | 5<br>5<br>5 | 5<br>5<br>5 |

TABLE 1D-continued

| Active compound | Pre-emergence test Active compound used in Kg/hectare | Oats | Wheat | Cotton | Sinapis | Cheno-podium | Echino-chloa |
|---|---|---|---|---|---|---|---|
| *(215) | 5<br>2.5<br>1.25 | 5<br>5<br>5 | 5<br>5<br>5 | 5<br>5<br>5 | 5<br>5<br>5 | 5<br>5<br>5 | 5<br>5<br>5 |
| *(194) | 5<br>2.5<br>1.25 | 5<br>5<br>5 | 5<br>5<br>4–5 | 5<br>5<br>4–5 | 5<br>5<br>5 | 5<br>5<br>5 | 5<br>5<br>5 |
| *(204) | 5<br>2.5<br>1.25 | 5<br>5<br>5 | 5<br>5<br>4–5 | 5<br>5<br>5 | 5<br>5<br>5 | 5<br>5<br>5 | 5<br>5<br>5 |
| *(191) | 5<br>2.5<br>1.25 | 5<br>5<br>5 | 5<br>5<br>4 | 5<br>5<br>5 | 5<br>5<br>5 | 5<br>5<br>5 | 5<br>5<br>5 |
| (192) | 5<br>2.5<br>1.25 | 5<br>4–5<br>4–5 | 4<br>4<br>4 | 5<br>4–5<br>4–5 | 5<br>5<br>5 | 5<br>5<br>5 | 5<br>5<br>5 |
| *(216) | 5<br>2.5<br>1.25 | 5<br>5<br>5 | 5<br>5<br>4–5 | 5<br>5<br>5 | 5<br>5<br>5 | 5<br>5<br>5 | 5<br>5<br>5 |
| *(217) | 5<br>2.5<br>1.25 | 5<br>5<br>5 | 5<br>5<br>4–5 | 5<br>5<br>5 | 5<br>5<br>5 | 5<br>5<br>5 | 5<br>5<br>5 |
| *(218) | 5<br>2.5<br>1.25 | 5<br>5<br>5 | 5<br>5<br>4 | 5<br>5<br>5 | 5<br>5<br>5 | 5<br>5<br>5 | 5<br>5<br>5 |

TABLE 1D-continued

| Active compound | | Pre-emergence test Active compound used in Kg/ hectare | Oats | Wheat | Cotton | Sinapis | Cheno- podium | Echino- chloa |
|---|---|---|---|---|---|---|---|---|
| *(220) | 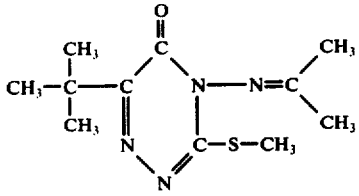 | 5<br>2.5<br>1.25 | 5<br>5<br>5 | 5<br>5<br>4–5 | 5<br>5<br>5 | 5<br>5<br>5 | 5<br>5<br>5 | 5<br>5<br>5 |
| *(221) | 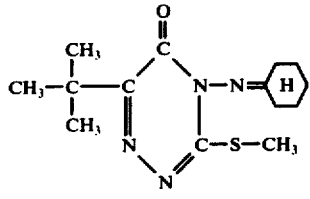 | 5<br>2.5<br>1.25 | 5<br>5<br>5 | 5<br>5<br>4–5 | 5<br>5<br>5 | 5<br>5<br>5 | 5<br>5<br>5 | 5<br>5<br>5 |
| (222) | 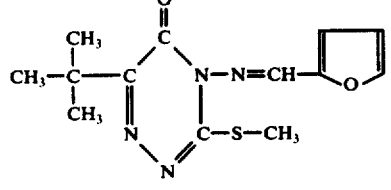 | 5<br>2.5<br>1.25 | 5<br>5<br>4–5 | 4–5<br>4<br>4 | 5<br>5<br>4–5 | 5<br>5<br>4–5 | 5<br>5<br>5 | 5<br>5<br>5 |
| (223) | 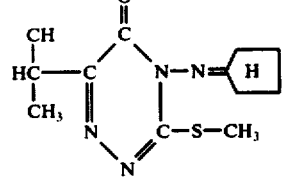 | 5<br>2.5<br>1.25 | 5<br>5<br>4–5 | 4–5<br>4–5<br>4 | 4–5<br>4–5<br>4 | 5<br>5<br>4–5 | 5<br>5<br>5 | 5<br>5<br>5 |
| *(224) | 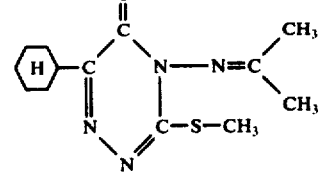 | 5<br>2.5<br>1.25 | 5<br>5<br>5 | 5<br>5<br>4–5 | 5<br>5<br>5 | 5<br>5<br>5 | 5<br>5<br>5 | 5<br>5<br>5 |
| (225) | 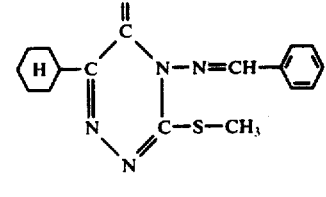 | 5<br>2.5<br>1.25 | 5<br>4<br>4 | 4<br>3<br>3 | 5<br>4–5<br>4 | 5<br>4<br>4 | 5<br>5<br>4 | 5<br>5<br>4–5 |
| (226) | 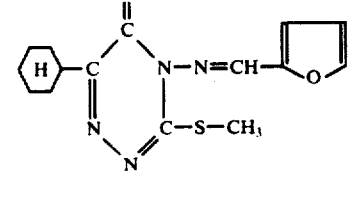 | 5<br>2.5<br>1.25 | 4–5<br>4<br>3 | 4<br>3<br>2 | 3–4<br>2<br>2 | 4<br>4<br>4 | 5<br>5<br>4 | 5<br>4–5<br>4 |

TABLE 1D-continued

| Active compound | | Pre-emergence test Active compound used in Kg/hectare | Oats | Wheat | Cotton | Sinapis | Chenopodium | Echinochloa |
|---|---|---|---|---|---|---|---|---|
| (227) | [structure: phenyl-C=N-N(N=CH-phenyl)-C(=O)...C-S-CH₃ triazinone] | 5<br>2.5<br>1.25 | 5<br>5<br>4 | 4–5<br>4–5<br>4 | 5<br>5<br>3 | 5<br>5<br>4–5 | 5<br>5<br>4 | 5<br>5<br>4–5 |
| (193) | [structure: triazinone with N-NH-CH(CCl₃)OH and S-CH₃] | 5<br>2.5<br>1.25 | 5<br>4–5<br>4 | 4–5<br>4<br>3 | 5<br>5<br>5 | 5<br>5<br>5 | 5<br>4–5<br>4 | 5<br>5<br>5 |
| (228) | [structure: triazinone with N=CH-phenyl and S-CH₃] | 5<br>2.5<br>1.25 | 4–5<br>3<br>2 | 4–5<br>4<br>3 | 5<br>3<br>2 | 5<br>5<br>4 | 5<br>5<br>5 | 5<br>5<br>5 |
| (229) | [structure: triazinone with N=CH-CH(CH₃)₂ and S-CH₃] | 5<br>2.5<br>1.25 | 5<br>4–5<br>4 | 4–5<br>4<br>4 | 4–5<br>4<br>4 | 5<br>4<br>4 | 5<br>5<br>4 | 5<br>5<br>4–5 |
| (100a) | [structure: phenyl triazinone with N-NH₂ and N-C₄H₉-n] | 40 | 2 | 2 | 3 | 2 | 5 | 2 |
| (102a) | [structure: phenyl triazinone with N-NH₂ and N-CH₂-phenyl] | 40 | 1 | 0 | 4 | 3 | 2 | 2 |
| **(172) | [structure: isopropyl triazinone with N-NH₂ and N-CH₃] | 5<br>2.5<br>1.25 | 5<br>5<br>5 | 5<br>5<br>5 | 5<br>5<br>5 | 5<br>5<br>5 | 5<br>5<br>5 | 5<br>5<br>5 |

TABLE 1D-continued

| Active compound | | Pre-emergence test Active compound used in Kg/ hectare | Oats | Wheat | Cotton | Sinapis | Cheno- podium | Echino- chloa |
|---|---|---|---|---|---|---|---|---|
| **(175) | (structure: 3-methyl-amino, tert-butyl triazinone) | 5<br>2.5<br>1.25 | 5<br>5<br>5 | 5<br>5<br>4 | 5<br>5<br>3 | 5<br>5<br>5 | 5<br>5<br>5 | 5<br>5<br>5 |
| **(176) | (structure: 3-ethyl-amino, tert-butyl triazinone) | 5<br>2.5<br>1.25 | 5<br>5<br>5 | 5<br>5<br>4 | 5<br>5<br>4 | 5<br>5<br>5 | 5<br>5<br>5 | 5<br>5<br>5 |
| (177) | (structure: 3-ethyl-amino, isopropyl triazinone) | 5<br>2.5<br>1.25 | 5<br>4-5<br>4 | 5<br>5<br>2 | 5<br>5<br>4 | 4-5<br>4<br>3 | 5<br>5<br>5 | 5<br>5<br>4 |
| (178) | (structure: 3-n-propyl-amino, isopropyl triazinone) | 5<br>2.5<br>1.25 | 3<br>3<br>2 | 2-3<br>1<br>1 | 2<br>2<br>1 | 4<br>3<br>2 | 3<br>3<br>2 | 3<br>2<br>2 |
| (179) | (structure: 3-allyl-amino, isopropyl triazinone) | 5<br>2.5<br>1.25 | 5<br>5<br>5 | 5<br>5<br>4 | 5<br>5<br>4 | 5<br>5<br>5 | 5<br>5<br>5 | 5<br>5<br>5 |
| **(180) | (structure: 3-dimethyl-amino, isopropyl triazinone) | 5<br>2.5<br>1.25 | 5<br>5<br>5 | 5<br>5<br>5 | 5<br>5<br>5 | 5<br>5<br>5 | 5<br>5<br>5 | 5<br>5<br>5 |
| (182) | (structure: 3-n-butyl-amino, cyclohexyl triazinone) | 40 | 4-5 | 4-5 | 5 | 5 | 5 | 5 |

TABLE 1D-continued

| Active compound | | Pre-emergence test Active compound used in Kg/hectare | Oats | Wheat | Cotton | Sinapis | Cheno-podium | Echino-chloa |
|---|---|---|---|---|---|---|---|---|
| **(232) | (structure: tert-butyl triazinone with N=C(CH₃)₂ and N-CH₃) | 5<br>2.5<br>1.25 | 5<br>5<br>4-5 | 5<br>5<br>4 | 5<br>5<br>5 | 5<br>5<br>5 | 5<br>5<br>5 | 5<br>5<br>5 |
| (230) | (structure: tert-butyl triazinone with N=CH-phenyl and N-CH₃) | 5<br>2.5<br>1.25 | 4-5<br>3<br>3 | 4-5<br>3<br>1 | 4-5<br>2<br>1 | 5<br>4-5<br>2 | 5<br>4-5<br>4 | 4-5<br>4-5<br>4 |
| (233) | (structure: tert-butyl triazinone with N=CH-C₆H₄-Cl and N-CH₃) | 5<br>2.5<br>1.25 | 4<br>3<br>2 | 3<br>1<br>0 | 3<br>2<br>1 | 5<br>4<br>3 | 5<br>4<br>3 | 4-5<br>4<br>2 |
| (231) | (structure: tert-butyl triazinone with N=CH-furyl and N-CH₃) | 40 | 5 | 5 | 5 | 5 | 5 | 5 |
| (9) | (structure: phenyl triazinone with N-NH₂ and N-CH₃) | 5<br>2.5<br>1.25 | 5<br>5<br>5 | 5<br>5<br>3 | 5<br>5<br>3 | 5<br>5<br>5 | 5<br>5<br>5 | 5<br>5<br>5 |
| (16) | (structure: phenyl triazinone with N-NH₂ and N(CH₃)₂) | 5<br>2.5<br>1.25 | 5<br>5<br>5 | 4-5<br>4-5<br>4-5 | 5<br>4-5<br>3 | 5<br>5<br>5 | 5<br>5<br>5 | 5<br>5<br>4-5 |
| (7) | (structure: phenyl triazinone with N-NH₂ and N-C₂H₅) | 5<br>2.5<br>1.25 | 5<br>4-5<br>4 | 5<br>5<br>4 | 4<br>3<br>1 | 5<br>5<br>5 | 5<br>5<br>5 | 5<br>5<br>4 |

TABLE 1D-continued

| Active compound | | Pre-emergence test Active compound used in Kg/hectare | Oats | Wheat | Cotton | Sinapis | Cheno-podium | Echino-chloa |
|---|---|---|---|---|---|---|---|---|
| (26) | [phenyl-triazinone with N—NH₂, N—H, C—N—CH₂CH=CH₂] | 5<br>2.5<br>1.25 | 5<br>4<br>3 | 4<br>3<br>2 | 3<br>3<br>3 | 5<br>4<br>3 | 5<br>3<br>2 | 4–5<br>2<br>1 |
| (25) | [phenyl-triazinone with N—NH₂ and C—N-pyrrolidinyl (CH₂—CH₂—CH₂—CH₂—CH₂)] | 5<br>2.5<br>1.25 | 1<br>0<br>0 | 2<br>1<br>0 | 2<br>1<br>0 | 4<br>2<br>1 | 3<br>2<br>1 | 2<br>1<br>1 |
| (234) | [phenyl-triazinone with N—NH—CH₃, C—O—CH₃] | 5<br>2.5<br>1.25 | 4–5<br>4<br>3 | 4<br>3<br>2 | 3<br>2<br>1 | 5<br>5<br>5 | 5<br>5<br>5 | 5<br>3<br>1 |

Notes:
*denotes higher activity than close known compounds 1a and 29a for typical new compounds of invention.
**denotes higher activity than close known compounds 100a and 102a for typical new compounds of invention.

EXAMPLE 26

The procedure of Example 2 is repeated, and the particular active compounds tested, the amounts applied, and the results obtained can be seen from the following Table 2E:

TABLE 2E

| Active compound | | Post-emergence test Active compound used in Kg/hectare | Oats | Wheat | Cotton | Sinapis | Cheno-podium | Stella-ria | Galin-soga | Echin-ochloa |
|---|---|---|---|---|---|---|---|---|---|---|
| (1a) | [phenyl-triazinone with N—NH₂, C—S—CH₃] | 2.4<br>1.2<br>0.6 | 4–5<br>4–5<br>1 | 2<br>1<br>0 | 5<br>5<br>5 | 5<br>5<br>5 | 5<br>5<br>5 | 5<br>5<br>5 | 5<br>5<br>5 | 5<br>5<br>5 |
| (29a) | [CH₃—C triazinone with N—NH₂, C—S—CH₃] | 2.4<br>1.2<br>0.6 | 5<br>4<br>3 | 3<br>2<br>0 | 5<br>5<br>5 | 5<br>5<br>5 | 5<br>5<br>5 | 5<br>5<br>3 | 5<br>5<br>4 | 5<br>5<br>4 |
| (22) | [C₂H₅—C triazinone with N—NH₂, C—SCH₃] | 2.4<br>1.2<br>0.6 | 4–5<br>4–5<br>4 | 3<br>3<br>2 | 5<br>5<br>5 | 5<br>5<br>5 | 5<br>5<br>5 | 5<br>5<br>4 | 5<br>5<br>5 | 5<br>5<br>5 |

TABLE 2E-continued

| Active compound | | Post-emergence test Active compound used in Kg/hectare | Oats | Wheat | Cotton | Sinapis | Chenopodium | Stellaria | Galinsoga | Echinochloa |
|---|---|---|---|---|---|---|---|---|---|---|
| *(21) | 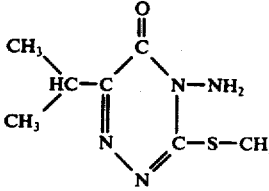 | 2.4<br>1.2<br>0.6 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 |
| *(147) | 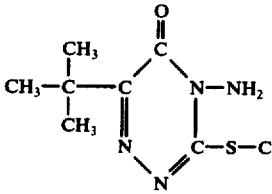 | 2.4<br>1.2<br>0.6 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 |
| *(11) | 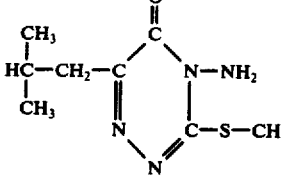 | 2.4<br>1.2<br>0.6 | 5<br>5<br>5 | 4-5<br>4<br>4 | 5<br>5<br>5 | 5<br>5<br>5 | 5<br>5<br>5 | 5<br>5<br>5 | 5<br>5<br>5 | 5<br>5<br>5 |
| *(23) | 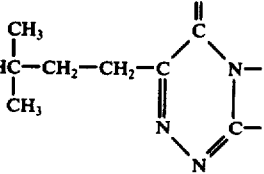 | 2.4<br>1.2<br>0.6 | 5<br>5<br>5 | 4-5<br>4<br>4 | 5<br>5<br>5 | 5<br>5<br>5 | 5<br>5<br>5 | 5<br>5<br>5 | 5<br>5<br>5 | 5<br>5<br>5 |
| (148) | 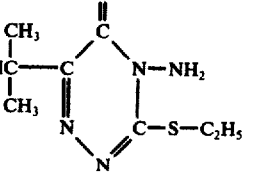 | 2.4<br>1.2<br>0.6 | 3<br>3<br>2 | 4-5<br>3<br>2 | 5<br>5<br>3 | 5<br>5<br>5 | 5<br>5<br>5 | 4-5<br>4<br>2 | 5<br>3<br>2 | 5<br>4-5<br>4-5 |
| (153) | 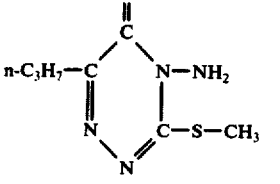 | 2.4<br>1.2<br>0.6 | 4-5<br>4<br>3 | 4<br>4<br>3 | 5<br>5<br>5 | 5<br>5<br>5 | 5<br>5<br>5 | 5<br>5<br>5 | 5<br>5<br>5 | 5<br>5<br>5 |
| (158) | 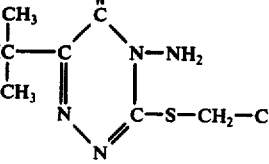 | 2.4<br>1.2<br>0.6 | 5<br>5<br>4 | 4<br>4<br>4 | 5<br>5<br>4 | 5<br>5<br>5 | 5<br>5<br>5 | 5<br>4-5<br>3 | 5<br>5<br>5 | 5<br>5<br>5 |

TABLE 2E-continued

| Active compound | | Post-emergence test Active compound used in Kg/hectare | Oats | Wheat | Cotton | Sinapis | Chenopodium | Stellaria | Galinsoga | Echinochloa |
|---|---|---|---|---|---|---|---|---|---|---|
| (163) | [structure: dihydropyran-triazinone with NH₂ and S-CH₃] | 2.4<br>1.2<br>0.6 | 5<br>4<br>4 | 5<br>4–5<br>3–4 | 5<br>5<br>4 | 5<br>5<br>5 | 5<br>5<br>4–5 | 5<br>5<br>5 | 5<br>4<br>2 | 4–5<br>3<br>3 |
| *(214) | [structure: isopropyl-triazinone with N=CH-CH(CH₃)₂ and S-CH₃] | 2.4<br>1.2<br>0.6 | 5<br>5<br>4–5 | 5<br>5<br>4 | 5<br>4–5<br>4–5 | 5<br>5<br>5 | 5<br>5<br>5 | 5<br>5<br>5 | 5<br>5<br>5 | 5<br>5<br>5 |
| (197) | [structure: isopropyl-triazinone with N=CH-cyclohexyl and S-CH₃] | 2.4<br>1.2<br>0.6 | 5<br>4<br>3 | 5<br>4–5<br>4 | 5<br>5<br>5 | 5<br>5<br>5 | 5<br>5<br>5 | 5<br>5<br>2 | 5<br>5<br>5 | 5<br>4–5<br>4 |
| (198) | [structure: isopropyl-triazinone with N=CH-phenyl and S-CH₃] | 2.4<br>1.2<br>0.6 | 4–5<br>4<br>3–4 | 4<br>3<br>1 | 5<br>5<br>5 | 5<br>5<br>5 | 5<br>5<br>5 | 5<br>5<br>4–5 | 5<br>5<br>5 | 5<br>5<br>5 |
| (206) | [structure: isopropyl-triazinone with N=CH-(o-tolyl) and S-CH₃] | 2.4<br>1.2<br>0.6 | 4–5<br>4<br>3 | 4<br>3–4<br>2 | 5<br>5<br>5 | 5<br>5<br>5 | 5<br>5<br>5 | 5<br>5<br>4–5 | 5<br>5<br>4 | 5<br>5<br>5 |
| (213) | [structure: isopropyl-triazinone with N=CH-(p-tolyl) and S-CH₃] | 2.4<br>1.2<br>0.6 | 4–5<br>3–4<br>3 | 5<br>3–4<br>2–3 | 5<br>5<br>5 | 5<br>5<br>5 | 5<br>5<br>5 | 5<br>5<br>4–5 | 5<br>5<br>5 | 5<br>5<br>4–5 |
| (207) | [structure: isopropyl-triazinone with N=CH-(p-OCH₃-phenyl) and S-CH₃] | 2.4<br>1.2<br>0.6 | 4–5<br>4<br>3 | 3–4<br>3–4<br>3 | 5<br>5<br>4–5 | 5<br>5<br>5 | 5<br>5<br>5 | 5<br>5<br>5 | 5<br>5<br>5 | 5<br>5<br>5 |

TABLE 2E-continued

| Active compound | | Active compound used in Kg/hectare | Oats | Wheat | Cotton | Sinapis | Chenopodium | Stellaria | Galinsoga | Echinochloa |
|---|---|---|---|---|---|---|---|---|---|---|
| (201) | [structure: 4-chlorobenzylidene triazinone] | 2.4<br>1.2<br>0.6 | 3<br>2<br>1 | 4<br>4<br>4 | 5<br>5<br>3 | 5<br>5<br>5 | 5<br>5<br>5 | 5<br>4–5<br>3 | 5<br>5<br>5 | 5<br>4–5<br>4 |
| (209) | [structure: 3-nitrobenzylidene triazinone] | 2.4<br>1.2<br>0.6 | 4–5<br>4<br>4 | 4<br>3<br>3 | 5<br>5<br>5 | 5<br>5<br>5 | 5<br>5<br>5 | 5<br>5<br>5 | 5<br>5<br>4 | 5<br>5<br>5 |
| (210) | [structure: 4-nitrobenzylidene triazinone] | 2.4<br>1.2<br>0.6 | 4<br>4<br>3 | 4<br>4<br>3 | 5<br>5<br>5 | 5<br>5<br>5 | 5<br>5<br>5 | 5<br>5<br>5 | 5<br>5<br>5 | 5<br>5<br>5 |
| (203) | [structure: furfurylidene triazinone] | 2.4<br>1.2<br>0.6 | 5<br>5<br>3 | 5<br>4–5<br>1 | 5<br>5<br>4 | 5<br>5<br>5 | 5<br>5<br>5 | 4–5<br>4<br>4 | 5<br>5<br>3 | 5<br>5<br>4 |
| *(215) | [structure: tert-butyl triazinone with isobutylidene] | 2.4<br>1.2<br>0.6 | 5<br>5<br>4 | 5<br>4–5<br>4 | 5<br>5<br>5 | 5<br>5<br>5 | 5<br>5<br>5 | 5<br>5<br>5 | 5<br>5<br>5 | 5<br>5<br>5 |
| (194) | [structure: isopropyl triazinone with isopropylidene] | 2.4<br>1.2<br>0.6 | 5<br>4<br>2 | 4–5<br>4–5<br>2 | 5<br>5<br>4–5 | 5<br>5<br>5 | 5<br>5<br>5 | 5<br>5<br>5 | 5<br>5<br>5 | 5<br>5<br>2 |
| (204) | [structure: cyclohexylidene triazinone] | 2.4<br>1.2<br>0.6 | 3<br>2<br>2 | 5<br>3<br>3 | 5<br>5<br>5 | 5<br>5<br>5 | 5<br>5<br>5 | 5<br>5<br>4–5 | 5<br>5<br>5 | 4<br>3<br>2 |

TABLE 2E-continued

| Active compound | | Post-emergence test Active compound used in Kg/hectare | Oats | Wheat | Cotton | Sinapis | Chenopodium | Stellaria | Galinsoga | Echinochloa |
|---|---|---|---|---|---|---|---|---|---|---|
| (191) | [structure: 6-isopropyl-3-methylthio-4-(N-(1-hydroxy-2,2,2-trichloroethyl)amino)-1,2,4-triazin-5(4H)-one] | 2.4<br>1.2<br>0.6 | 3<br>3<br>2 | 3<br>3<br>1 | 2<br>1<br>1 | 5<br>4-5<br>4 | 4<br>3<br>2 | 3<br>2<br>1 | 3<br>2<br>1 | 5<br>4<br>3 |
| (192) | [structure: 6-tert-butyl-3-methylthio-4-(N-(1-hydroxy-2,2,2-trichloroethyl)amino)-1,2,4-triazin-5(4H)-one] | 2.4<br>1.2<br>0.6 | 4-5<br>4<br>3 | 4<br>4<br>4 | 5<br>5<br>5 | 5<br>5<br>5 | 5<br>5<br>5 | 5<br>5<br>5 | 5<br>5<br>5 | 5<br>5<br>5 |
| *(216) | [structure: 6-isopropyl-3-methylthio-4-(propylideneamino)-1,2,4-triazin-5(4H)-one] | 2.4<br>1.2<br>0.6 | 5<br>5<br>5 | 5<br>5<br>4 | 5<br>5<br>5 | 5<br>5<br>5 | 5<br>5<br>5 | 5<br>5<br>5 | 5<br>5<br>5 | 5<br>5<br>5 |
| *(217) | [structure: 6-isopropyl-3-methylthio-4-(butylideneamino)-1,2,4-triazin-5(4H)-one] | 2.4<br>1.2<br>0.6 | 5<br>5<br>4 | 5<br>5<br>4 | 5<br>5<br>5 | 5<br>5<br>5 | 5<br>5<br>5 | 5<br>5<br>5 | 5<br>5<br>5 | 5<br>5<br>5 |
| *(218) | [structure: 6-isopropyl-3-methylthio-4-(3-phenylpropylideneamino)-1,2,4-triazin-5(4H)-one] | 2.4<br>1.2<br>0.6 | 5<br>5<br>4 | 5<br>5<br>4 | 5<br>5<br>5 | 5<br>5<br>5 | 5<br>5<br>5 | 5<br>5<br>5 | 5<br>5<br>5 | 5<br>5<br>5 |
| *(220) | [structure: 6-tert-butyl-3-methylthio-4-(isopropylamino)-1,2,4-triazin-5(4H)-one] | 2.4<br>1.2<br>0.6 | 5<br>5<br>3 | 5<br>5<br>4 | 5<br>5<br>5 | 5<br>5<br>5 | 5<br>5<br>5 | 5<br>5<br>5 | 5<br>5<br>5 | 5<br>5<br>5 |
| (221) | [structure: 6-tert-butyl-3-methylthio-4-(cyclohexylideneamino)-1,2,4-triazin-5(4H)-one] | 2.4<br>1.2<br>0.6 | 5<br>3<br>3 | 4-5<br>4<br>4 | 5<br>5<br>5 | 5<br>5<br>5 | 5<br>5<br>5 | 5<br>5<br>3 | 5<br>5<br>3 | 5<br>5<br>5 |

TABLE 2E-continued

| Active compound | | Active compound used in Kg/hectare | Oats | Wheat | Cotton | Sinapis | Chenopodium | Stellaria | Galinsoga | Echinochloa |
|---|---|---|---|---|---|---|---|---|---|---|
| (222) | [structure] | 2.4<br>1.2<br>0.6 | 5<br>4<br>3 | 4–5<br>4<br>4 | 5<br>5<br>5 | 5<br>5<br>5 | 5<br>5<br>5 | 5<br>5<br>4–5 | 5<br>5<br>5 | 5<br>5<br>5 |
| (223) | [structure] | 2.4<br>1.2<br>0.6 | 3<br>2<br>1 | 4<br>4<br>3 | 5<br>4–5<br>3 | 5<br>4<br>3 | 5<br>4–5<br>4 | 5<br>2<br>1 | 5<br>1<br>1 | 5<br>4–5<br>4 |
| (224) | [structure] | 2.4<br>1.2<br>0.6 | 5<br>4–5<br>4 | 4–5<br>4–5<br>4 | 5<br>5<br>5 | 5<br>5<br>5 | 5<br>5<br>4 | 5<br>5<br>4 | 5<br>3<br>2 | 5<br>5<br>5 |
| (225) | [structure] | 2.4<br>1.2<br>0.6 | 4–5<br>3<br>2 | 5<br>4<br>3–4 | 5<br>4<br>3 | 5<br>5<br>5 | 5<br>5<br>4 | 5<br>5<br>2 | 4<br>3<br>2 | 5<br>5<br>4–5 |
| (226) | [structure] | 2.4<br>1.2<br>0.6 | 4–5<br>4<br>3 | 5<br>4<br>3 | 4–5<br>3<br>3 | 5<br>5<br>5 | 5<br>5<br>5 | 5<br>5<br>4 | 3<br>2<br>1 | 5<br>5<br>5 |
| (227) | [structure] | 2.4<br>1.2<br>0.6 | 4<br>3<br>2 | 4–5<br>4<br>3 | 3<br>3<br>3 | 5<br>5<br>5 | 4–5<br>4<br>2 | 4–5<br>3<br>1 | 1<br>1<br>1 | 5<br>5<br>3 |
| (193) | [structure] | 2.4<br>1.2<br>0.6 | 5<br>4–5<br>4 | 4–5<br>4<br>3 | 5<br>5<br>5 | 5<br>5<br>5 | 5<br>5<br>5 | 5<br>5<br>5 | 5<br>5<br>3 | 5<br>5<br>4 |

TABLE 2E-continued

| Active compound | Active compound used in Kg/hectare | Oats | Wheat | Cotton | Sinapis | Chenopodium | Stellaria | Galinsoga | Echinochloa |
|---|---|---|---|---|---|---|---|---|---|
| (228) | 2.4 | 5 | 5 | 5 | 5 | 5 | 5 | 5 | 5 |
|  | 1.2 | 4-5 | 4-5 | 5 | 5 | 5 | 4 | 4 | 5 |
|  | 0.6 | 3 | 4-5 | 3 | 5 | 5 | 4 | 2 | 4-5 |
| *(229) | 2.4 | 5 | 5 | 5 | 5 | 5 | 5 | 5 | 5 |
|  | 1.2 | 5 | 5 | 5 | 5 | 5 | 5 | 5 | 5 |
|  | 0.6 | 5 | 5 | 5 | 5 | 5 | 5 | 5 | 5 |
| (100a) | 10 | 2 | 2-3 | 2-3 | 5 | 3 | — | — | 2-3 |
| (102a) | 10 | 1 | 1 | 2-3 | 4 | 3 | — | — | 1 |
| **(172) | 2.4 | 5 | 5 | 5 | 5 | 5 | 5 | 5 | 5 |
|  | 1.2 | 5 | 5 | 5 | 5 | 5 | 5 | 5 | 5 |
|  | 0.6 | 5 | 5 | 5 | 5 | 5 | 5 | 5 | 5 |
| (175) | 2.4 | 5 | 4-5 | 5 | 5 | 5 | 5 | 5 | 5 |
|  | 1.2 | 4-5 | 4 | 5 | 5 | 5 | 5 | 5 | 4-5 |
|  | 0.6 | 4-5 | 4 | 5 | 5 | 5 | 5 | 5 | 4-5 |
| (176) | 2.4 | 4 | 5 | 5 | 5 | 5 | 5 | 5 | 4-5 |
|  | 1.2 | 4 | 3 | 4 | 5 | 5 | 5 | 5 | 3 |
|  | 0.6 | 3 | 2 | 4 | 5 | 5 | 4-5 | 4 | 3 |

TABLE 2E-continued

| Active compound | | Post-emergence test Active compound used in Kg/hectare | Oats | Wheat | Cotton | Sinapis | Chenopodium | Stellaria | Galinsoga | Echinochloa |
|---|---|---|---|---|---|---|---|---|---|---|
| (177) | [structure: 6-isopropyl triazinone with N—NH₂ and N—C₂H₅] | 2.4<br>1.2<br>0.6 | 4–5<br>3<br>2 | 4–5<br>2<br>2 | 4<br>3<br>2 | 5<br>5<br>5 | 5<br>5<br>5 | 4<br>4<br>1 | 4–5<br>4<br>3 | 4<br>3<br>1 |
| (178) | [structure with N—C₃H₇-n] | 2.4<br>1.2<br>0.6 | 1<br>1<br>0 | 2<br>1<br>0 | 2<br>1<br>1 | 5<br>4<br>3 | 4<br>3<br>3 | 2<br>0<br>0 | 1<br>0<br>0 | 2<br>1<br>0 |
| (179) | [structure with N—CH₂—CH=CH₂] | 2.4<br>1.2<br>0.6 | 4<br>2<br>2 | 3<br>2<br>2 | 4<br>3<br>2 | 5<br>5<br>5 | 5<br>5<br>4–5 | 5<br>4–5<br>2 | 5<br>4<br>2 | 4<br>2<br>2 |
| (180) | [structure with N(CH₃)₂] | 2.4<br>1.2<br>0.6 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 |
| (182) | [structure with cyclohexyl and N—C₄H₉-n] | 10 | 4 | 4 | 3 | 5 | 5 | — | — | 4–5 |
| **(232) | [structure with t-butyl and N—N=C(CH₃)₂, N—CH₃] | 2.4<br>1.2<br>0.6 | 5<br>5<br>5 | 5<br>4–5<br>4 | 5<br>5<br>5 | 5<br>5<br>5 | 5<br>5<br>5 | 5<br>5<br>5 | 5<br>5<br>5 | 5<br>5<br>5 |
| (230) | [structure with t-butyl and N—N=CH—phenyl, N—CH₃] | 2.4<br>1.2<br>0.6 | 4–5<br>4<br>2 | 5<br>4<br>4 | 5<br>5<br>2 | 5<br>5<br>5 | 5<br>5<br>5 | 5<br>5<br>4–5 | 5<br>5<br>5 | 4–5<br>4–5<br>4 |

TABLE 2E-continued

| Active compound | | Post-emergence test Active compound used in Kg/hectare | Oats | Wheat | Cotton | Sinapis | Chenopodium | Stellaria | Galinsoga | Echinochloa |
|---|---|---|---|---|---|---|---|---|---|---|
| (233) | [structure: 4-chlorobenzylidene triazinone] | 2.4<br>1.2<br>0.6 | 4-5<br>4-5<br>4 | 5<br>4-5<br>4-5 | 4-5<br>4<br>4 | 5<br>5<br>5 | 5<br>5<br>5 | 5<br>5<br>5 | 5<br>5<br>5 | 5<br>5<br>5 |
| (231) | [structure: furfurylidene triazinone] | 10 | 5 | 5 | 5 | 5 | 5 | — | — | 5 |
| **(9) | [structure: phenyl triazinone with N-NH₂ and N-CH₃] | 2.4<br>1.2<br>0.6 | 5<br>5<br>4 | 5<br>4<br>2 | 5<br>5<br>5 | 5<br>5<br>5 | 5<br>5<br>5 | 5<br>5<br>5 | 5<br>5<br>5 | 5<br>5<br>5 |
| **(16) | [structure: phenyl triazinone with N-NH₂ and N(CH₃)₂] | 2.4<br>1.2<br>0.6 | 5<br>5<br>4 | 5<br>4-5<br>4 | 5<br>5<br>5 | 5<br>5<br>5 | 5<br>5<br>5 | 5<br>5<br>5 | 5<br>5<br>5 | 5<br>5<br>5 |
| (7) | [structure: phenyl triazinone with N-NH₂ and N-C₂H₅] | 2.4<br>1.2<br>0.6 | 5<br>3<br>2 | 2<br>1<br>0 | 5<br>5<br>4 | 5<br>5<br>5 | 5<br>5<br>5 | 5<br>5<br>4 | 5<br>5<br>5 | 5<br>5<br>4 |
| (26) | [structure: phenyl triazinone with N-NH₂ and N-CH₂CH=CH₂] | 2.4<br>1.2<br>0.6 | 5<br>3<br>2 | 1<br>1<br>1 | 4<br>3<br>1 | 5<br>5<br>5 | 5<br>5<br>4-5 | 5<br>2<br>1 | 5<br>5<br>5 | 3<br>3<br>3 |
| (25) | [structure: phenyl triazinone with N-NH₂ and pyrrolidinyl] | 10 | 0 | 1 | 0 | 4-5 | 3-4 | — | — | 1 |

TABLE 2E-continued

| Active compound | | Post-emergence test Active compound used in Kg/hectare | Oats | Wheat | Cotton | Sinapis | Chenopodium | Stellaria | Galinsoga | Echinochloa |
|---|---|---|---|---|---|---|---|---|---|---|
| (234) | [structure: phenyl-C(=O)-N(NH-CH₃)-C(=N-N)-O-CH₃] | 2.4 | 5 | 2 | 5 | 5 | 5 | 5 | 5 | 5 |
| | | 1.2 | 4 | 1 | 3 | 5 | 5 | 5 | 5 | 5 |
| | | 0.6 | 3 | 0 | 0 | 5 | 5 | 5 | 5 | 5 |

NOTES:
*denotes higher activity than close known compounds 1a and 29a for typical new compounds of invention.
**denotes higher activity than close known compounds 100a and 102a for typical new compounds of invention.

I. GENERIC INVENTION

Advantageously, in accordance with the present invention, in the foregoing formulae, as the case may be: R repesents I. straight and branched chain aliphatic hydrocarbon having 1-18, particularly 1-10 or 1-8 or 1-6 or 1-5 or 1-4 or 1-3 or 1-2, more particularly 2-18 or 3-18 or 4-18 or 5-18 or 6-18, etc., and even 2-8 or 2-6 or 2-5 or 2-4 or 2-3, carbon atoms; including methyl, ethyl, n-propyl, isopropyl, n-butyl, isobutyl, tert-butyl, amyl, isoamyl, hexyl, isohexyl, heptyl, octyl, isoctyl, nonyl, decyl, undecyl, dodecyl, tridecyl, tetradecyl, pentadecyl, hexadecyl, heptadecyl, octadecyl, and the like, especially straight and branched chain alkyl having 1-18, particularly 1-10 or 1-8 or 1-6 or 1-5 or 1-4 or 1-3 or 1-2, more particularly 2-18 or 3-18 or 4-18 or 5-18 or 6-18, etc., and even 2-8 or 2-6 or 2-5 or 2-4 or 2-3, carbon atoms, preferably 1-6 carbon atoms, more especially lower alkyl, and most especially alkyl having 1-8 or 1-6 or 1-5 or 1-4, or 2-8 or 2-6 or 25, or even 3-5 branched, carbon atoms; further including vinyl, α-, β- and γ-allyl- i.e. propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, and the like, especially straight and branched chain alkenyl having 2-18 carbon atoms, preferably 2-6 carbon atoms, more especially lower alkenyl, and most especially alkenyl having 2-4 carbon atoms; and still further including acetylenyl, propynyl, butynly, pentynyl, hexaynyl, heptynyl, octynyl, nonynyl, decynyl, undecynyl, dodecynyl, tridecynyl, tetradecynyl, pentadecynyl, hexadecynyl, heptadecynyl, octadecynyl, and the like, especially straight and branched chain alkynyl having 2-18 carbon atoms, preferably 2-6 carbon atoms, more especially lower alkynyl, and most especially alkynyl having 2-4 carbon atoms;

II. cycloaliphatic hydrocarbon having 5-10 or 5-8 or 5-6 ring carbon atoms, including cyclopentyl, cyclohexyl, cycloheptyl, cyclooctyl, admantyl, cyclopentenyl, cyclohexenyl, cycloheptenyl, cyclooctenyl, cyclopenynyl, cyclohexynyl, cyclooctynyl, and the like, especially cycloalkyl having 5-10 ring carbon atoms and tricycloalkyl having 10 ring carbon atoms, and most especially cycloalkyl having 5-8 or 5-6 ring carbon atoms and adamantyl;

III. araliphatic hydrocarbon having 6-10 ring carbon atoms and 1-4 aliphatic carbon atoms, including phenyl- and naphthyl- methyl, ethyl, n-propyl, isopropyl, n-butyl, isobutyl, sec-butyl, tert-butyl, vinyl, allyl, butenyl, acetylenyl, propynyl, butynyl, and the like, especially mono- and di- nuclear $C_{6-10}$ aryl substituted $C_{1-4}$ straight and branched chain aliphatic hydrocarbon and most especially phenyl- and napthyl-substitued $C_{1-4}$ alkyl, $C_{2-4}$ alkenyl, and $C_{2-4}$ alkynyl;

IV. aryl hydrocarbon having 6-10 ring carbon atoms, including phenyl, naphthyl, and the like, especially mono- and dinuclear $C_{6-10}$ aryl hydrocarbon;

V. heterocyclic and heterocyclic-lower alkyl (e.g. heterocyclic-$C_{1-4}$ or $C_{1-3}$ or $C_{1-2}$ alkyl) correspondingly having 5-6 ring members including at least one hetero linking atom, e.g. 1-3 hetero atoms, such as oxygen, nitrogen, and/or sulfur, including α- and β- furyl, di- and tetra- hydrofuryl, furfuryl, dioxanyl, pyranyl, dihydropyranyl, tetrahydropyranyl, dioxinyl, especially p- or 1,4-dioxinyl, dioxazolyl, especially 1,2,3-dioxazolyl, morpholino, thioxanyl, especially p- or 1,4-thioxanyl, pyrazolyl, pyrrolinyl, especially $\Delta^2$-pyrrolin-1-yl, pyrrolidino, piperidyl, especially piperidino, pyridyl, pyridyl-methyl, pyrazolyl, pyrazolinyl, especially $\Delta^2$-pyrazolin-1-yl, pyrazolidinyl, especially pyrazolidine-1-yl, pyridazinyl, pyrimidinyl, especially 1,2-dihydropyrimidinyl, pyrrodiazolyl, especially 1,2,5-pyrrodiazol-1-yl, thiophenyl (especially thienyl), thiophanyl, thiazolyl, especially o-thiazolyl, thiazolinyl, thiazolidinyl, especially o-thiazolidin-2-yl and p-thiazolidin-3-yl, thiazinyl, especially o-thiazinyl and p-thiazinyl, thiodiazinyl, especially 1,3,4,2-thiodiazinyl, thiodiazolyl, especially 1,2,3-thiodiazolyl, thiodiazolidinyl, especially 1,2,3-thiodiazolidin-2-yl, and the like, and preferably furyl, pyridyl, and thienyl; as well as VI. all of such aliphatic, cycloaliphatic, araliphatic, aryl, heterocyclic and heterocyclic-lower alkyl set forth under (I), (II), (III), (IV) and (V) above which are mono, di and poly (same and mixed) substituted, e.g. mono to tetra substituted, with substituents including halo, such as chloro, bromo, iodo and fluoro; nitro, carboloweralkoxy such as carbo-(methyl to tert-butyl inclusive, and the like, as noted above) -oxy, especially carboalkoxy having 1-6, and preferably 1-5, carbon atoms, and most especially carboalkoxy having 1-4 carbon atoms in the alkoxy moiety; lower alkyl such as methyl to tert-butyl inclusive as noted above, especially $C_{1-4}$ alkyl; lower alkoxy sych as methoxy, ethoxy, n-propoxy, isopropoxy, n-butoxy, isobutoxy, sec-butoxy, tert-butoxy, and the like, especially $C_{1-4}$ alkoxy; aryl lower alkylmercapto such as mono- and di-nuclear $C_{6-10}$ aryl substituted lower alkyl mercapto, especially $C_{6-10}$ aryl- $C_{1-4}$ akylmercapto, and particularly phenyl- and naphthyl- (methyl to tert-butyl inclusive, and the like, as noted above) mercapto; lower alkyl mercapto such as (methyl to tert-butyl inclusive, and the like, as noted above) mercapto, and especially $C_{1-4}$ alkyl mercapto; $C_{6-10}$ aryl mercapto such as phenyl- and naphthyl-mercapto; and the like, especially mono- and di-nuclear arylmercapto having 6–10 ring carbon atoms; $C_{6-10}$ aryloxy such as phenoxy, naphthyloxy, and the like, especially mono- and di-nuclear aryloxy having 6–10 ring carbon atoms;

$R_1$ and $R_2$ each respectively represents vii. hydrogen;

viii. alkyl having 1–12 carbon atoms such as methyl to dodecyl inclusive, and the like, as noted above, especially lower alkyl, and most especially $C_{1-4}$ alkyl;

ix. alkanoyl having 1–6 carbon atoms such as formyl, acetyl, propionyl, butyryl, pentanoyl, hexanoyl, and the like, especially $C_{1-5}$, preferably $C_{1-4}$, and even $C_{2-5}$ or $C_{2-4}$, alkyl carbonyl; as well as x. all such alkyl and alkanoyl set forth under (viii) and ix above which are mono, di and poly (same and mixed) substituted, with substituents including cyano, hydroxy, and halo such as chloro, bromo, iodo and/or fluoro;

with the proviso that $R_1$ and $R_2$ when taken together represent xi. alkylidene hydrocarbon having 1–12 or 1–8 or 1–6 carbon atoms including methylidene, ethylidene, n-propylidene, isopropylidene, n-butylidene, isobutylidene, sec-butylidene, pentylidene, 3-methyl-but-2-ylidene, hexyliden, 3,3-dimethyl-but-2-ylidene, 2-ethyl-hex-1-ylidene, and the like, especially lower alkylidene, and more especially $C_{1-4}$ alkylidene;

xii. cycloalkylidene hydrocarbon having 5–8 ring carbon atoms including cyclopentylidene, cyclohexylidene, cycloheptylidene, cyclooctyliden, and the like, especially cycloloweralkylidene and more especially cyclo $C_{5-6}$ alkylidene; as well as xiii. all such alkylidene and cycloalkylidene set forth under (xi) and (xii) above which are mono, di and poly (same and mixed) substituted, e.g. mono to tetra substituted, with substituents such as cycloalkyl having 5–8 ring carbon atoms such as cyclopentyl, cyclohexyl, cycloheptyl, cyclooctyl, and the like, especially $C_{5-6}$ cycloalkyl; aryl having 6–10 ring carbon atoms, including phenyl, naphthyl, and the like, especially mono- and di- nuclear $C_{6-10}$ aryl; haloaryl having 6–10 ring carbon atoms, including halo, i.e., chloro, bromo, iodo and/or fluoro, -phenyl, -naphthyl, and the like, especially mono- and di-nuclear halo $C_{6-10}$ aryl; nitroaryl having 6–10 ring carbon atoms, including nitrophenyl, nitronaphthyl, and the like, especially mono- and di-nuclear nitro $C_{6-10}$ aryl; lower alkyl aryl having 6–10 ring carbon atoms including methyl to tert-butyl inclusive and the like, substituted -phenyl, - naphthyl, and the like, especially mono- and di-nuclear $C_{1-4}$ alkyl $C_{6-10}$ aryl; lower alkoxy aryl having 6–10 ring carbon atoms including methoxy to tert-butoxy inclusive, and the like, substituted -phenyl, -naphthyl, and the like, especially mono- and di- nuclear $C_{1-4}$ alkoxy $C_{6-10}$ aryl; halo-nitro-aryl having 6–10 ring carbon atoms, including halo, i.e., chloro, bromo, iodo and/or fluoro, -nitro-, -phenyl, -naphthyl, and the like, especially mono- and di-nuclear halo-nitro-$C_{6-10}$ aryl; arylloweralkenyl having 6–10 ring carbon atoms, including phenyl-, naphthyl-, and the like, substituted -vinyl, α-, β- and γ-allyl, butenyl, and the like, especially mono- and di- nuclear $C_{6-10}$ aryl-$C_{2-4}$ straight and branched alkenyl; and heterocyclic and nitro-substituted heterocyclic correspondingly having 5–6 ring members including at least one hetero linking atoms as set forth under (v) above and particularly furyl, nitrofuryl and pyridyl; and with the further proviso that $R_1$ and $R_2$ when taken together with the adjacent nitrogen atom repesent N-containing heterocyclic having 5–6 ring members as set forth under (v) above, and particularly morpholino and piperidino;

Y represents oxygen, sulfur or $-\overset{|}{N}-R_4$; and $R_3 R_4$, as the case may be, each respectively represents xiv. hydrogen xv. aliphatic hydrocarbon having 1–18 carbon atoms as set forth under (i) above;

xvi. cycloaliphatic hydrocarbon having 5–8 ring carbon atoms as set forth under (ii) above;

xvii. araliphatic hydrocarbon having 6–10 ring carbon atoms and 1–4 aliphatic carbon atoms as set forth under (iii) above;

xviii. aryl hydrocarbon having 6–10 ring carbon atoms as set forth under (iv) above; as well as (xix). all such aliphatic, cycloaliphatic, araliphatic, and aryl set forth under (xv), (xvi), (xvii) and (xviii) above which are mono, di and poly (same and mixed) substituted, e.g. mono to tetra substituted, with substituents such as halo, including chloro, bromo, iodo and fluoro; amino including unsubstituted amino and lower alkyl substituted amino as N-lower alkyl and N,N-dilower alkyl amino, especially having 1–4 carbon atoms in each correspondingly alkyl moiety, and particularly methyl to tert-butyl inclusive as noted above; nitro; lower alkyl such as methyl to tert-butyl inclusive as noted above, and especially $C_{1-4}$ alkyl; lower alkoxy such as methoxy to tert-butoxy inclusive as noted above, and especially $C_{1-4}$ alkoxy; lower alkylmercapto such as methyl to tert-butyl inclusive, and the like, -mercapto, and especially $C_{1-4}$ alkylmercapto; aryloxy having 6–10 ring carbon atoms such as phenoxy, naphthyloxy, and the like, especially mono- and di-nuclear $C_{6-10}$ aryloxy; and haloaryl-mercapto having 6–10 ring carbon atoms such as chloro, bromo, iodo and fluoro, -phenyl, -naphthyl, and the like, -mercapto, especially mono- and di- nuclear halo $C_{6-10}$ arylmercapto;

with the proviso that $R_3$ and $R_4$ when taken together with the adjacent nitrogen atom repesent N-containing heterocyclic having 5–6 ring members as set forth under (v) above, and particularly morpholino and piperidino; and with the further proviso that when Y is oxygen $R_3$ may also be lower alkanoyl such as formyl, acetyl, propionyl, butyryl, pentanoyl, and the like, especially alkanoyl having 1–6 or 1–5, preferably 1–4, carbon atoms, or even 2–5 or 2–4 carbon atoms.

I (S). GENERIC INVENTION

When Y is S, preferably:

R is $C_{1-18}$ aliphatic, $C_{5-10}$ cycloaliphatic, $C_{6-10}$ aryl-$C_{1-4}$ aliphatic, $C_{6-10}$ aryl, heterocyclic or heterocyclic-lower alkyl having 5–6 ring members in the corresponding heterocyclic moiety with 1–3 hetero linking atoms such as O, N and/or S, or such aliphatic, cycloaliphatic, aryl-aliphatic, aryl, heterocyclic-arkyl, respectively, which is substituted with 1–4 or 1–3 or 1–2 (or even 1) same or mixed substituents, i.e. at least one substituent, such as halo, nitro, carbo-lower alkoxy, lower alkyl, lower alkoxy, $C_{6-10}$ aryl-lower alkylmercapto and/or $C_{6-10}$ arylmercapto;

$R_1$ and $R_2$ each individually is hydrogen, $C_{1-12}$ alkyl or $C_{1-6}$ alkanoyl, or such alky and alkanoyl, respectively, which is substituted with 1-4 or 1-3 or 1-2 (or even 1) same or mixed substituents, i.e. at least one substituent, such as hydroxy and/or halo;

with the proviso that $R_1$ and $R_2$ when taken together represent $C_{1-12}$ alkylidene or $C_{5-8}$ cycloalkylidene, or such alkylidened and cycloalkylidene, respectively, which is substituted with 1-4 or 1-3 or 1-2 (or even 1) same as mixed substituents, i.e. at least one substituent, such as $C_{5-8}$ cycloalkyl, $C_{6-10}$ aryl, $C_{6-10}$ haloaryl, lower alkyl-$C_{6-10}$ aryl, lower alkoxy-$C_{6-10}$ aryl, nitro-$C_{6-10}$ aryl, halo-nitro-$C_{6-10}$ aryl, $C_{6-10}$ aryl-lower alkenyl, heterocyclic and/or nitro-heterocyclic, with the corresponding heterocyclic moiety having 5-6 ring members with 1-3 hetero linking atoms such as O, N and/or S; and with the further proviso that $R_1$ and $R_2$ when taken together with the adjacent N-atom form an N-containing heterocyclic moiety having 5-6 ring members; and $R_3$ is hydrogen, $C_{1-18}$ aliphatic, C;hd 5-8 cycloaliphatic, $C_{6-10}$ aryl-$C_{1-4}$ aliphatic or $C_{6-10}$ aryl, or such aliphatic, cycloaliphatic, aryl-aliphatic and aryl, respectively, which is substituted with 1-4 or 1-3 or 1-2 (or even 1) same or mixed substituents, i.e. at least one substituent, such as halo, amino, lower alkyl substituted amino, nitro, lower alkyl, lower alkoxy, lower alkylmercapto, $C_{6-10}$ aryloxy and/or halo $C_{6-10}$ arylmercapto.

I ($-\overset{|}{N}-R_4$). GENERIC INVENTION

When Y is $-\overset{|}{N}-R_4$, preferably:

R is $C_{1-18}$ aliphatic, $C_{5-10}$ cycloaliphatic, $C_{6-10}$ aryl-$C_{1-4}$ aliphatic, $C_{6-10}$ aryl or heterocyclic having 5-6 ring members with 1-3 hetero linking atoms and as O,N and/or S, or such aliphatic, cycloaliphatic, aryl-aliphatic, aryl and heterocyclic, respectively, which is substituted with 1-4 or 1-3 or 1-2 (or even 1) same or mixed substituents, i.e. at least one substituent such as halo, nitro, carbo-lower alkoxy, lower alkoxy, lower alkylmercapto, $C_{6-10}$ arylmercapto and/or $C_{6-10}$ aryloxy;

$R_1$ and $R_2$ each individually is hydrogen;

with the proviso that $R_1$ and $R_2$ when taken together represent $C_{1-12}$ alkylidene, or such alkylidene which is substituted with 1-4 or 1-3 or 1-2 (or even 1) same or mixed substituents, i.e. at least one substituent, such as $C_{6-10}$ aryl, $C_{6-10}$ haloaryl and/or heterocyclic having 5-6 ring members with 1-3 hetero linking atoms such as O, N and/or S; and with the further proviso that $R_1$ and $R_2$ together with the adjacent N-atom form an N-containing heterocyclic moiety having 5-6 ring members; and $R_3$ and $R_4$ each individually is hydrogen, $C_{1-18}$ aliphatic, $C_{5-8}$ cycloaliphatic, $C_{6-10}$ aryl-$C_{1-4}$ aliphatic or $C_{6-10}$ aryl, or such aliphatic, cycloaliphatic, aryl-aliphatic, and aryl, respectively, which is substituted with 1-4 or 1-3 or 1-2 (or even 1) same or mixed substituents, i.e. at least one substituent, such as halo, amino, lower alkyl substituted amino, nitro, lower alkyl, lower alkoxy and/or $C_{6-10}$ aryloxy;

with the proviso that $R_3$ and $R_4$ when taken together with the adjacent N-atom form an N-containing heterocyclic moiety having 5-6 ring members.

I (O). GENERIC INVENTION

When Y is O, preferably:

R is $C_{1-18}$ aliphatic, $C_{5-10}$ cycloaliphatic, $C_{6-10}$ aryl-$C_{1-4}$ aliphatic or $C_{6-10}$ aryl;

$R_1$ and $R_2$ each individually is hydrogen, $C_{1-12}$ alkyl or $C_{1-6}$ alkanoyl, or such alkyl and alkanoyl, respectively, which is substituted with 1-4 or 1-3 or 1-1 (or even 1) same or mixed substituents, i.e. at least one substituent, such as cyano, hydroxy and/or halo, especially hydroxy and/or halo;

with the proviso that $R_1$ and $R_2$ when taken together represent $C_{1-12}$ alkylidene or $C_{5-8}$ cycloalkylidene, or such alklidene and cycloalkylidene, respectively, which is substituted with 1-4 or 1-3 or 1-2 (or even 1) substituents, i.e. at least one substituent, such as $C_{6-10}$ aryl; and $R_3$ is lower alkanoyl, hydrogen, $C_{1-18}$ aliphatic, $C_{5-8}$ cycloaliphatic, $C_{6-10}$ aryl-$C_{1-4}$ aliphatic or $C_{6-10}$ aryl, or such aliphatic, cycloaliphatic, aryl-aliphatic and aryl, respectively, which is substituted with 1-4 or 1-3 or 1-2 (or even 1) same or mixed substituents, i.e. at least one substituent, such as halo, amino, lower alkyl substituted amino, nitro, lower alkyl, lower alkoxy and/or $C_{6-10}$ aryloxy.

II. SUBGENERIC INVENTION

Y is O, S and $-\overset{|}{N}-R_4$, and preferable: R is $C_{1-8}$ alkyl, $C_{2-8}$ alkenyl, $C_{3-8}$ alkynyl, $C_{5-10}$ cycloalkyl, phenyl-$C_{1-4}$ alkyl, phenyl-$C_{2-4}$ alkenyl, napthyl-$C_{1-4}$ alkyl, naphthyl-$C_{2-4}$ alkenyl, furyl-$C_{1-4}$ alkyl, pyridyl-$C_{1-4}$ alkyl, phenyl, naphthyl, furyl, pyranyl, pyridyl or thienyl, or such alkyl, alkenyl, alkynyl, cycloalkyl, phenyl-alkyl, phenyl-alkenyl, naphthyl-alkyl, naphthyl-alkenyl, furyl-alkyl, pryidyl-alkyl, phenyl, naphtyl, furyl, pryanyl, pyridyl and thienyl, respectively, which is substituted with 1-4 or 1-3 or 1-2 (or even 1) same or mixed substituents, i.e. at least one substituent, such as chloro, bromo, fluoro, iodo, nitro, carbo-$C_{1-4}$ alkoxy, $C_{1-4}$ alkyl, $C_{1-4}$ alkoxy, phenyl-$C_{1-4}$ alkylmercapto, $C_{1-4}$ alkylmercapto, phenylmercapto, naphthylmercapto, phenoxy and/or naphthyloxy;

$R_1$ and $R_2$ each individually is hydrogen, $C_{1-4}$ alkyl or $C_{2-5}$ alkanoyl, or such alkyl and alkanoyl, respectively, which is substitued with 1-4 or 1-3 or 1-2 (or even 1) same or mixed substituents, i.e. at least one substituent, such as cyano, hydroxy and/or halo;

with the proviso that $R_1$ and $R_2$ when taken together represent $C_{1-8}$ alkylidene or $C_{5-6}$ cycloalkylidene, or such alkylidene and cycloalkylidene, respectively, which is substituted with 1-4 or 1-3 or 1-2 (or even 1) same or mixed substituents, i.e. at least one substituent, such as $C_{5-6}$ cycloalkyl, phenyl, naphthyl, halophenyl, halonaphthyl, $C_{1-4}$ alkylphenyl, $C_{1-4}$ alkyl naphthyl, $C_{1-4}$ alkoxy phenyl, $C_{1-4}$ alkoxy naphthyl, nitrophenyl, nitronaphthyl, chloro-nitro-phenyl, chloro-nitro-naphthyl, phenyl-$C_{2-4}$ alkenyl, naphthyl-$C_{2-4}$ alkenyl, furyl, nitro-furyl and/or pyridyl; and $R_3$ and $R_4$ each individually is hydrogen, $C_{1-18}$ alkyl, $C_{2-6}$ alkenyl, $C_{2-6}$ alkynyl, $C_{5-6}$ cycloalkyl, phenyl $C_{1-4}$ alkyl, phenyl $C_{2-4}$ alkenyl, naphthyl $C_{1-4}$ alkyl, naphthyl-$C_{2-4}$ alkenyl, phenyl or naphthyl, or such alkyl, alkenyl, alkynyl, cycloalkyl, phenylalkyl, phenyl-alkenyl, naphthyl-alkyl, naphthyl-alkenyl, phenyl and naphthyl, respectively, which is substituted with 1-4 or 1-3 or 1-2 (or even 1) same or mixed substituents, i.e. at least one substituent, such as chloro, bromo, fluoro, iodo, amino, $C_{1-4}$ alkylamino, di-$C_{1-4}$ alkyl-amino, nitro, $C_{1-4}$ alkyl, $C_{1-4}$ alkoxy, $C_{1-4}$ alkylmercapto, phenyloxy, naphthyloxy, chlorophenylmercapto and/or chloro-naphthylmercapto;

with the proviso that $R_3$ and $R_4$ when taken together with the adjacent N-atom form an N-containing heterocyclic moiety having 5-6 ring members such as morpholino or piperidino; and with the further proviso that when Y is O then $R_3$ is also $C_{2-4}$ alkanoyl.

II (S). SUBGENERIC INVENTION

When Y is S, preferably:

R is $C_{1-6}$ alkyl, $C_{5-10}$ cycloalkyl, phenyl-$C_{1-4}$ alkyl, phenyl-$C_{2-4}$ alkenyl, furyl-$C_{1-4}$ alkyl, pyridyl-$C_{1-4}$ alkyl, phenyl, naphthyl, furyl, pyranyl or thienyl, or such alkyl, cycloalkyl, phenyl-alkyl, phenyl alkenyl, furyl-alkyl, pryidyl-alkyl, phenyl, naphthyl, furyl, pyranyl and thienyl, respectively, which is substituted with 1—4 or 1–3 or 1–2 (or even 1) same or mixed substituents, i.e. at least one substituent, such as chloro, bromo, fluoro, iodo, nitro, carbo-$C_{1-4}$ alkoxy, $C_{1-4}$ alkyl, $C_{1-4}$ alkoxy and/or phenyl-$C_{1-4}$ alkylmercapto;

$R_1$ and $R_2$ each individually is hydrogen, $C_{1-4}$ alkyl or $C_{2-5}$ alkanoyl, or such alkyl and alkanoyl, respectively, which is substituted with 1–4 or 1–3 or 1–2 (or even 1 ) same or mixed substituents, i.e. at least one substituent, such as hydroxy and/or halo;

with the proviso that $R_1$ and1 $R_2$ when taken together represent $C_{1-8}$ alkylidene or $C_{5-6}$ cycloalkylidene, or such alkylidene and cycloalkylidene, respectively, which is substituted with 1–4 or 1–3 or 1–2 (or even 1) same or mixed substituents, i.e. at least one substituent, such as $C_{5-6}$ cycloalkyl, phenyl, naphthyl, halophenyl, halonaphthyl, $C_{1-4}$ alkyl-phenyl, $C_{1-4}$ alkyl-naphthyl, $C_{1-4}$ alkoxy-phenyl, $C_{1-4}$alkoxy-naphthyl, nitrophenyl, nitronaphthyl, chloro-nitro-phenyl, chloro-nitro-naphthyl, phenyl-$C_{2-4}$ alkenyl, naphthyl-$C_{2-4}$ alkenyl, furyl, nitro-furyl and/or pyridyl; and $R_3$ is hydrogen, $C_{1-18}$ alkyl, $C_{2-6}$ alkenyl, $C_{2-6}$ alkynyl, $C_{5-6}$ cycloalkyl, phenyl-$C_{1-4}$ alkyl, phenyl-$C_{1-4}$ alkenyl, naphthyl-$C_{1-4}$ alkyl, naphthyl-$C_{2-4}$ alkenyl, phenyl, or naphthyl or such alkyl, alkenyl, alkynyl, cycloalkyl, phenyl-alkyl, phenyl-alkenyl, naphthyl-alkyl, naphthyl-alkenyl, phenyl and naphthyl, respectively, which is substituted with 1–4 or 1–3 or 1–2 (or even 1) same or mixed substituents, i.e. at least one substituent such as chloro, bromo, fluro, iodo, amino, $C_{1-4}$ alkylamino, di-$C_{1-4}$ alkyl-amino, nitro, $C_{1-4}$ alkyl, $C_{1-4}$ alkoxy, $C_{1-4}$ alkylmercapto, phenoxy, naphthyloxy, chloro-phenylmercapto and/or chloro-naphthylmercapto.

II (—N—$R_4$). SUBGENERIC INVENTION

When Y is —N—$R_4$, preferably:

R is $C_{1-6}$ alkyl, $C_{2-6}$ alkenyl, $C_{2-6}$ alkynyl, $C_{5-10}$ cycloalkyl, phenyl-$C_{1-4}$ alkyl, phenyl, furyl or pyridyl, or such alkyl, alkenyl, alkynyl, cycloalkyl, phenyl-alkyl, phenyl, furyl and pyridyl, respectively, which is substituted with 1–4 or 1–3 or 1–2 (or even 1) same or mixed substituents, i.e. at least one substituent, such as chloro, bromo, fluoro, iodo, nitro, carbo-$C_{1-4}$ alkoxy, $C_{1-4}$ alkoxy, $C_{1-4}$ alkylmercapto, phenylmercapto, naphtylmercapto, phenyloxy and/or naphthyloxy;

$R_1$ and $R_2$ each respectively is hydrogen;

with the proviso that $R_1$ and $R_2$ when taken together represent $C_{1-8}$ alkylidene, or such alkyklidene which is substituted with 1–4 or 1–3 or 1–2 (or even 1) same or mixed substituents, i.e. at least one substituent, such as phenyl, naphthyl, halo-phenyl, halonaphthyl and/or furyl; and $R_3$ and $R_4$ each respectively is hydrogen, $C_{1-18}$ alkyl, $C_{2-6}$alkenyl, $C_{5-6}$cycloalkyl, phenyl-$C_{1-4}$alkyl or phenyl, or such alkyl, alkenyl, cycloalkyl, phenyl-alkyl and phenyl, respectively, which is substituted with 1–4 or 1–3 or 1–2 (or even 1) same or mixed substituents, i.e. at least one substituent, such as chloro, bromo, fluoro, iodo, amino, $C_{1-4}$ alkylamino, di-$C_{1-4}$ alkyl-amino, nitro, $C_{1-4}$ alkyl, $C_{1-4}$ alkoxy, phenoxy and/or naphthyloxy;

with the proviso that $R_3$ and $R_4$ when taken together with the adjacent N-atom form an N-containing heterocyclic moiety having 5–6 ring members such as morpholino or piperidino.

II (O). SUBGENERIC INVENTION

When Y is O, preferably:

R is $C_{1-6}$ alkyl, $C_{2-6}$ alkenyl, $C_{2-6}$ alkynyl, $C_{5-10}$ cycloalkyl, phenyl-$C_{1-4}$ alkyl, phenyl-$C_{2-4}$ alkenyl, naphthyl-$C_{1-4}$ alkyl, naphthyl-$C_{2-4}$ alkenyl, phenyl or naphthyl;

$R_1$ and $R_2$ each individually is hydrogen, $C_{1-4}$ alkyl or $C_{2-5}$ alkanoyl, or such alkyl and alkanoyl, respectively, which is substituted with 1–4 or 1–3 or 1–2 (or even 1) same or mixed substituents, i.e. at least one substituent, such as cyano, hydroxy and/or halo;

with the proviso that $R_1$ and $R_2$ when taken together represent $C_{1-18}$ alkylidene or $C_{5-6}$ cycloalkylidene, or such alkylidene and cycloalkylidene, respectively, which is substituted with 1–4 or 1–3 or 1–2 (or even 1) substituents, i.e. at least one substituent, such as phenyl; and $R_3$ is $C_{2-4}$ alkanoyl, hydrogen, $C_{1-18}$ alkyl, $C_{2-6}$ alkenyl, $C_{2-6}$ alkynyl, $C_{5-6}$ cycloalkyl, phenyl-$C_{1-4}$ alkyl, naphthyl-$C_{1-4}$ alkyl, phenyl or naphthyl, or such alkyl, alkenyl, alkynyl, cycloalkyl, phenyl-alkyl, naphthyl-alkyl, phenyl and naphthyl, respectively, which is substituted with 1–4 or 1–3 or 1–2 (or even 1) same or mixed substituents, i.e. at least one substituent, such as chloro, bromo, fluoro, iodo, amino, $C_{1-4}$ alkylamino, di-$C_{1-4}$ alkyl-amino, nitro, $C_{1-4}$ alkoxy, phenoxy and/or naphthyloxy.

III. PREFERRED EMBODIMENT

Y is O, S and —N—$R_4$, and preferably:

R is $C_{1-6}$ alkyl, cyclohexyl, adamantyl, phenyl-$C_{1-4}$ alkyl, phenyl-$C_{2-4}$ alkenyl, phenyl, furyl, pyranyl, furfuryl, pyridylmethyl, $C_{2-4}$ carbo alkoxy-$C_{1-4}$ alkyl, phenyl-$C_{1-4}$ alkylmercapto-$C_{1-4}$ alkyl, chlorophenyl-$C_{1-4}$ alkyl, $C_{1-4}$ alkoxy-phenyl, chlorophenyl or nitrophenyl;

$R_1$ and $R_2$ each individually is hydrogen, $C_{1-4}$ alkyl, $C_{2-4}$ alkanoyl or chloro-hydroxy-$C_{1-4}$ alkyl;

with the proviso that $R_1$ and $R_2$ when taken together represent /$C_{1-8}$ alkylidene, cyclopentylidene, cyclohexylidene, cyclohexyl-$C_{1-4}$ alkylidene, phenyl-$C_{1-4}$ alkyklidene, styryl-$C_{1-4}$ alkylidene, chlorophenyl-$C_{1-4}$ alkylidene, $C_{1-4}$ alkyl-phenyl-$C_{1-4}$ alkylidene, $C_{1-4}$ alkoxy-phenyl-$C_{1-4}$ alkylidene, nitrophenyl-$C_{1-4}$ alkylidene, chloronitro-phenyl-$C_{1-4}$alkylidene, furyl-$C_{1-4}$alkylidene, nitrofuryl-$C_{1-4}$ alkylidene or pyridyl-$C_{1-4}$ alkylidene; and $R_3$ and $R_4$ each individually is hydrogen, $C_{1-18}$ alkyl, $C_{2-4}$ alkenyl, $C_{2-4}$ alkynyl, cyclohexyl, phenyl, phenyl-$C_{1-4}$ alkyl, chloro-$C_{2-4}$ alkenyl, di-$C_{1-4}$ alkyl-amino-$C_{1-4}$ alkyl, $C_{1-4}$ alkyl-mercapto-$C_{1-4}$ alkyl, chlorophenyl-$C_{1-4}$ alkyl, chlorophenylmercapto-$C_{1-4}$ alkyl or chlorophenyl;

with the proviso that $R_3$ and $R_4$ when taken together with the adjacent N-atom form a morpholino or piperidino group; and with the further proviso that when Y is O then $R_3$ is also $C_{2-4}$ alkanoyl.

III (S). PREFERRED EMBODIMENT

When Y is S, preferably:

R is $C_{1-6}$ alkyl, cyclohexyl, adamantyl, phenyl-$C_{1-4}$ alkyl, phenyl-$C_{2-4}$ alkenyl, phenyl, furyl, pyranyl, furfuryl, pryidyl-methyl, $C_{2-4}$ carbo-alkoxy-$C_{1-4}$ alkyl, phenyl-$C_{1-4}$ alkylmercapto-$C_{1-4}$ alkyl, chlorophenyl-$C_{1-4}$ alkyl, $C_{1-4}$ alkyl-phenyl, $C_{1-4}$ alkoxy-phenyl, chlorophenyl or nitrophenyl.

$R_1$ and $R_2$ each individually is hydrogen, $C_{1-4}$ alkyl, $C_{2-4}$ alkanoyl or chloro-hydroxy-$C_{1-4}$ alkyl;

with the proviso that $R_1$ and $R_2$ when taken together represent $C_{1-18}$ alkylidene, cyclopentylidene, cyclohexylidene, cyclohexyl-$C_{1-4}$ alkylidene, phenyl-$C_{1-4}$ alkylidene, styryl-$C_{1-4}$ alkylidene, chlorophenyl-$C_{1-4}$ alkylidene, $C_{1-4}$ alkyl-phenyl-$C_{1-4}$ alkylidene, $C_{1-4}$ alkoxy-phenyl-$C_{1-4}$ alkylidene, nitrophenyl-$C_{1-4}$ alkylidene, nitrofuryl-$C_{1-4}$ alkylidene or pyridyl-$C_{1-4}$ alkylidene; and $R_3$ is hydrogen, $C_{1-18}$ alkyl, $C_{2-4}$ alkynyl, cyclohexyl, phenyl-$C_{1-4}$ alkyl, chloro-$C_{2-4}$ alkenyl, di-$C_{1-4}$ alkylamino-$C_{1-4}$ alkyl $C_{1-4}$ alkylmercapto-$C_{1-4}$ alkyl, chlorophenyl-$C_{1-4}$ alkyl or chlorophenylmercapto-$C_{1-4}$ alkyl.

III (—N—$R_4$). PREFERRED EMBODIMENT

When Y is —N—$R_4$, preferably:

R is $C_{1-6}$ alkyl, cyclohexyl, phenyl, chlorophenyl-$C_{1-4}$ alkyl or chlorophenyl;

$R_1$ and $R_2$ each individually is hydrogen;

with the proviso that $R_1$ and $R_2$ when taken together represent $C_{1-8}$ alkylidene, phenyl-$C_{1-4}$ alkylidene, chlorophenyl-$C_{1-4}$ alkylidene or furyl-$C_{1-4}$ alkylidene; and $R_3$ and $R_4$ each individually is hydrogen, $C_{1-18}$ alkyl, $C_{2-4}$ alkenyl, phenyl, phenyl-$C_{1-4}$ alkyl, di-$C_{1-4}$ alkylamino-$C_{1-4}$ alkyl, chlorophenyl-$C_{1-4}$ alkyl or chlorophenyl;

with the proviso that $R_3$ and $R_4$ when taken together with the adjacent N-atom form a morpholino or piperidino group.

III (O). PREFERRED EMBODIMENT

When Y is O, preferably:

R is $C_{1-6}$ alkyl, cyclohexyl, phenyl-$C_{1-4}$ alkyl or phenyl;

$R_1$ and $R_2$ each individually is hydrogen, $C_{1-4}$ alkyl, $C_{2-4}$ alkanoyl or chloro-hydroxy-$C_{1-4}$ alkyl; and $R_3$ is $C_{2-4}$ alkanoyl, hydrogen, $C_{1-18}$ alkyl, $C_{2-4}$ alkenyl, $C_{2-4}$ alkynyl, chloro-$C_{2-4}$ alkenyl or di-$C_{1-4}$ alkyl-amino-$C_{1-4}$ alkyl.

IV. PARTICULAR EMBODIMENT

Y is O, S or —N—$R_4$, and preferably:

A. when Y is O,

R is $C_{1-5}$ alkyl, $C_{5-6}$ cycloalkyl, phenyl or phenyl-$C_{1-4}$ alkyl;

$R_1$ and $R_2$ each individually is hydrogen, $C_{1-4}$ alkyl, $C_{2-5}$ alkanoyl or hydroxy-trichloro-$C_{2-4}$ alkyl; and $R_3$ is hydrogen, $C_{1-8}$ alkyl, $C_{2-4}$ alkenyl, $C_{2-4}$ alknyl, dichloro-$C_{2-4}$ alkenyl, di-$C_{1-4}$ alkyl-amino-$C_{1-4}$alkyl or $C_{2-5}$ alkanoyl;

B. when Y is S,

R is $C_{1-8}$ or $C_{2-8}$ alkyl, $C_{5-10}$ cycloalkyl, $C_{1-4}$ alkoxy-carbonyl-$C_{1-4}$ alkyl, optionally phenyl, chlorophenyl, $C_{1-4}$ alkyl-phenyl, $C_{1-4}$ alkoxy-phenyl, nitrophenyl, phenyl-$C_{1-4}$ alkyl, chlorophenyl-$C_{1-4}$ alkyl, phenyl-$C_{2-4}$ alkenyl, phenyl-$C_{1-4}$ alkylmercapto-$C_{1-4}$ alkyl, furyl, furfuryl, pyranyl or pyridylmethyl;

$R_1$ and $R_2$ each individually is hydrogen, $C_{1-4}$ alkyl, $C_{2-5}$ alkanoyl or hydroxy-trichloro-$C_{2-4}$ alkyl;

With the proviso that $R_1$ and $R_2$ when taken together represent $C_{1-12}$ alkylidene, $C_{5-6}$ cycloalkylidene, $C_{5-6}$ cycloalkyl-$C_{1-4}$ alkylidene, phenyl-$C_{1-4}$ alkylidene, phenyl-$C_{2-6}$ alkenylidene, mono and di chloro-phenyl-$C_{1-4}$ alkylidene, $C_{1-4}$ alkyl-phenyl-$C_{1-4}$ alkylidene, $C_{1-4}$ alkoxy-phenyl-$C_{1-4}$ alkylidene, nitro-phenyl-$C_{1-4}$ alkylidene, chloro-nitro-phenyl-$C_{1-4}$alkylidene, furfurylidene, nitro-furfurylidene or pyridyl-methylidene; and $R_3$ is hydrogen, $C_{1-18}$ alkyl, $C_{2-4}$ alkenyl, $C_{2-4}$ alkynyl, dichloro-$C_{2-4}$ alkenyl, di-$C_{1-4}$ alkyl-amino-$C_{1-4}$ alkyl, $C_{1-4}$ alkylmercapto-$C_{1-4}$ alkyl, $C_{5-6}$ cycloalkyl, phenyl-$C_{1-4}$ alkyl, chlorophenyl-$C_{1-4}$ alkyl or chlorophenylmercapto-$C_{1-4}$ alkyl; and C. When Y is —N—$R_4$, R is $C_{1-5}$ or $C_{2-5}$ alkyl, $C_{5-6}$ cycloalkyl, optionally phenyl, chlorophenyl or chlorophenyl-$C_{1-4}$ alkyl;

$R_1$ and $R_2$ each individually is hydrogen;

With the proviso that $R_1$ and $R_2$ when taken together represent $C_{1-4}$ alkylidene, phenyl-$C_{1-4}$ alkylidene, chloro-phenyl-$C_{1-4}$ alkylidene or furfurylidene; and $R_3$ and $R_4$ each individually is hydrogen, $C_{1-18}$ or $C_{1-4}$ alkyl, $C_{2-4}$ alkenyl, di-$C_{1-4}$ alkyl-amino-$C_{1-4}$ alkyl, phenyl, mono and di chloro-phenyl, phenyl-$C_{1-4}$ alkyl or chlorophenyl-$C_{1-4}$ alkyl;

With the proviso that $R_3$ and $R_4$ when taken together with the adjacent N-atom form optionally a morpholino group or a piperidino group, i.e. 3-oxa-pentamethylene or pentamethylene attached at the corresponding terminal carbon atoms to said N-atom.

V. MORE PARTICULAR EMBODIMENT

Y is O, S or —N—$R_4$, and preferably:

A'. when Y is O,

R is $C_{1-5}$ alkyl, cyclohexyl, phenyl or benzyl;

$R_1$ is hydrogen, $C_{1-4}$ alkyl, acetyl or 1-hydroxy-2,2,2-trichloro-ethyl;

$R_2$ is hydrogen or acetyl; and $R_3$ is hydrogen, $C_{1-6}$ alkyl, $C_{2-4}$ alkenyl, $C_{2-4}$ alkynyl, dichloro-$C_{2-4}$ alkenyl, di-$C_{1-4}$ alkyl-amino-$C_{1-4}$ alkyl or acetyl;

B'. when Y is S,

R is $C_{1-6}$ or $C_{2-6}$ alkyl, cyclohexyl, adamantyl, $C_{1-4}$ alkoxy-carbonyl-methyl, optionally phenyl, chlorophenyl, $C_{1-4}$ alkyl-phenyl, $C_{1-4}$ alkoxy-phenyl, nitrophenyl, benzyl, chlorobenzyl, styryl, benzylmercaptomethyl, furyl, furfuryl, pyranyl or pyridyl-methyl;

$R_1$ is hydrogen, $C_{1-4}$ alkyl, acetyl or 1-hydroxy-2,2,2-trichloro-ethyl;

$R_2$ is hydrogen, $C_{1-4}$ alkyl or acetyl;

With the proviso that $R_1$ and $R_2$ when taken together represent $C_{1-8}$ alkylidene, $C_{5-6}$ cycloalkylidene, hexahydrobenzylidene, phenyl-$C_{1-4}$ alkylidene, cinnamylidene, mono and di chloro-benzylidene, $C_{1-4}$ alkyl-benzylidene, $C_{1-4}$ alkoxy-benzylidene, nitro-benzylidene, chloronitro-benzylidene, furfurylidene, nitro-furfurylidene or pyridyl-methylidene; and $R_3$ is hydrogen, $C_{1-18}$ alkyl, $C_{2-4}$ alkenyl, $C_{2-4}$ alkynyl, dichloro-$C_{2-4}$ alkenyl, di-$C_{1-4}$ alkyl-amino-$C_{1-4}$ alkyl, $C_{1-4}$ alkylmercapto-$C_{1-4}$ alkyl, cyclohexyl, benzyl, chlorobenzyl or chlorophenylmercaptomethyl; and C'. when Y is —N—$R_4$, R is $C_{1-5}$ or $C_{2-5}$ alkyl, cyclohexyl, optionally phenyl, chlorophenyl or chlorobenzyl;

$R_1$ and $R_2$ each individually is hydrogen;

With the proviso that $R_1$ and $R_2$ when taken together represent $C_{1-4}$ alkylidene, benzylidene, chloro-benzylidene or furfurylidene;

$R_3$ is hydrogen, $C_{1-18}$ alkyl, $C_{2-4}$ alkenyl, di-C1-4; 1 alkyl-amino-$C_{1-4}$ alkyl, phenyl, mono and di chlorophenyl, benzyl or chloro-benzyl; and $R_4$ is hydrogen or $C_{1-4}$ alkyl;

With the proviso that $R_3$ and $R_4$ when taken together with the adjacent N-atom form optionally a morpholino group or a piperidino group, i.e. 3-oxa-pentamethylene or pentamethylene attached at the corresponding terminal carbon atoms to said N-atom.

VI. SPECIAL EMBODIMENT

In accordance with a special embodiment of compounds having surprisingly higher herbicidal properties, Y is S or $-N-R_4$, and R is $C_{2-5}$ alkyl or cyclohexyl;
$R_1$ is hydrogen or 1-hydroxy-2,2,2-trichloro-ethyl;
$R_2$ is hydrogen;
With the proviso that $R_1$ and $R_2$ when taken together represent $C_{3-4}$ alkylidene or cyclohexylidene;
$R_3$ is $C_{1-4}$ alkyl; and
$R_4$ is hydrogen or $C_{1-4}$ alkyl.

VII. PREFERRED SPECIAL EMBODIMENT

In accordance with a preferred case of such special embodiment of compounds having surprisingly higher herbicidal properties, Y is S or $-N-R_4$, and R is $C_{3-5}$ branched alkyl or cyclohexyl;
$R_1$ is hydrogen or 1-hydroxy-2,2,2-trichloro-ethyl;
$R_2$ is hydrogen;
With the proviso that $R_1$ and $R_2$ when taken together represent $C_{3-4}$ branched alkylidene or cyclohexylidene;
$R_3$ is $C_{1-2}$ alkyl; and
$R_4$ is hydrogen or methyl.

VIII. NEW COMPOUNDS

With specific reference to the particular new compounds of the present invention, considering the foregoing definitions, especially under I— GENERIC INVENTION:

a. when Y is O,
R, $R_1$, $R_2$ and $R_3$ are the same as defined under (i) through (xix) above, respectively, as the case may be, with the proviso that $R_3$ may also be lower alkanoyl such as formyl, acetyl, propionyl, butyryl, pentanoyl, and the like, and especially alkanoyl having 1-5 or 2-5, preferably 1-4 or 2-4, carbon atoms;

b. when Y is S, and $R_1$, $R_2$ and $R_3$ are the same as defined under (a) immediately above,
R is the same as defined under (a) immediately above, with the proviso that when R is aliphatic in accordance with (i) above, said aliphatic always has at least 2, or at least 3, or at least 4, or at least 5, or at least 6, or more, and up to 18 carbon atoms and preferably has 2-6, 3-6, 4-6, or 5-6 ;1 and up to 18 carbon atoms, and with the further proviso that when R is aryl in accordance with (iv) above, such aryl is always substituted aryl which is substituted in accordance with (vi) above;

c. when Y is S, and R, $R_1$ and $R_2$ are the same as defined under (a) immediately above,
$R_3$ is the same as defined under (xv) through (xix) above, respectively, with the proviso that when $R_3$ is aliphatic in accordance with (xv) above, such aliphatic always has at least 2, or at least 3, or at least 4, or at least 5, or at least 6, or more and up to 18 carbon atoms, and preferably has 2-6, 3-6, 4-6, or 5-6 and up to 18 carbon atoms;

d. when Y is S, and R and $R_3$ are the same as defined under (a) immediately above,
$R_1$ and $R_2$ each respectively is the same as defined under (viii), (ix) and (x) above, as the case way be, with the proviso that $R_1$ and $R_2$ taken together represent alkylidene or cycloalkylidene as defined under (xi) through (xiii) above, with the optional preferred proviso that such alkylidene when substituted with aryl having 6-10 carbon atoms always has at least 2, or at least 3, or at least 4, or at least 5, or at least 6, or more and up to 18 carbon atoms, and preferably has 2-6, 3-6, 4-6, or 5-6 and up to 18 carbon atoms;

e. when Y is $-N-R_4$, and $R_1$, $R_2$ and $R_3$ are the same as defined under (a) immediately above,
R is the same as defined under (b) immediately above, and
$R_4$ is defined individually in the same way as $R_3$ is defined wherein $R_3$ and $R_4$ may be alike or different, with the proviso that $R_3$ and $R_4$ when taken together with the adjacent nitrogen atom represent N-containing heterocyclic as defined under (v) above;

(f) when Y is $-N-R_4$, and R and $R_3$ are the same as defined under (a) immediately above,
$R_1$ and $R_2$ each respectively is the same as defined under (viii) through (xiii) above, as the case may be, and
$R_4$ is the same as defined under (c) immediately above, with the proviso that $R_3$ and $R_4$ when taken together with the adjacent nitrogen atom represent N-containing heterocyclic as defined under (v) above; and (g) when Y is $-N-R_4$, and R, $R_1$ and $R_2$ are the same as defined under (a) immediately above;
$R_3$ and $R_4$ each respectively is the same as defined under (xv), (xvi), (xvii), (xviii) and (xix) above, as the case may be, with the proviso that $R_4$ may also be hydrogen and that when $R_4$ is hydrogen $R_3$ is aliphatic as defined under (i) above but having always only 1-3 carbon atoms, or cycloaliphatic as defined under (ii) above, or substituted -aliphatic having 1-18 carbon atoms, -cycloaliphatic, -araliphatic or -aryl as defined under (i), (ii), (iii), (iv) when taken together with (xix), as the case may be, and with the further proviso that $R_3$ and $R_4$ when taken together with the adjacent nitrogen atom represent heterocyclic as defined under (v) above but always excluding oxygen as hetero atom.

Similarly, analogous coverage to that defined under I (S)— GENERIC INVENTION through VII— PREFERRED SPECIAL EMBODIMENT is intended for the instant new compounds; i.e. all cases where, when Y is S, R is not methyl or is not phenyl, or $R_1$ and $R_2$ are both rot simultaneously hydrogen, or $R_3$ is not methyl; or where, when Y is $-N-R_4$, R is not methyl or is not phenyl, or $R_1$ and $R_2$ are both not simultaneously hydrogen, or $R_3$ and $R_4$ are not simultaneously hydrogen, or when $R_4$ is hydrogen $R_3$ is at most $C_{1-3}$ alkyl, or not phenyl, or not benzyl, or $R_3$ and $R_4$ when taken together withethe adjacent N-atom do not form morpholino.

It will be realized that as used herein the term "ylidene-amino" is meant to be synonymous with the term "ylidene-imino" so as to cover the hydrocarbyl-amino or hydrocarbyl-imino linkages $-CH=N-$ and

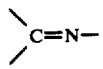

as the case may be (cf. the corresponding linkages of compounds 14, 15, 17-19, 27, 28, 35, 119-124, 127 and 194-233 for

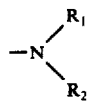

when $R_1$ and $R_2$ are taken together). These linkages are to be distinguished from N-containing heterocyclic linkages of certain of the instant compounds (cf. the corresponding linkages of compounds 125, 126 and 128–133 for

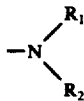

when $R_1$ and $R_2$ are taken together with the adjacent N-atom, as well as those of compounds 13a, 25, 133 and 168 for

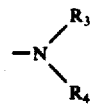

when $R_3$ and $R_4$ are taken together with the adjacent N-atom).

A preferred sub-group of compounds in accordance with the invention includes those of formula (I) wherein Y is S, R is branched lower alkyl or cycloalkyl, $R_3$ is lower alkyl, and $R_1$ and $R_2$ are individually hydrogen or taken together are cycloalkylidene having 5–8 ring carbon atoms or alkylidene having 1–12 carbon atoms substituted with aryl having 6–10 ring carbon atoms or furyl, pyridyl, thienyl, pyrryl, chinolyl, thiazolyl, imidazolyl or indyl. Especially preferred are those wherein R is branched butyl, e.g. tert.-butyl, $R_3$ is methyl, and $R_1$ and $R_2$ are individually hydrogen or taken together are cyclopentylidene, cyclohexylidene or lower alkylidene substituted with phenyl, furyl, nitrophenyl, lower alkyl phenyl or lower alkoxy phenyl, e.g. cyclohexylidene, banzylidene, nitrofurfurylidene, and the like.

Thus, 3-methylthio-4-(cyclohexylidene-amino)-6-tert.-butyl-1,2,4-triazine-5-one (221) shows very good general herbicidal activity on post-emergence and for pre-emergence is selective for soybeans, i.e. it will prevent growth of most plants and weeds but not of soybeans.

The very similar cyclopentyl compound (223), m.p. 78° C., is similarly useful, as is the corresponding furfuryl-idene-2 compound (222), and can be prepared in the same manner as in Example 22.

2-methylthio-4-(benzylidene-amino)-6-tert.-butyl-1,2,4-triazine-5-one (236) has the same general properties and is also selective as to cotton and tomatoes on pre-emergence application. It is also effective in growing corn, potatoes, millet and peanuts applied to the extent of 0.3–2 kg/hectare. Surprisingly the compound also exhibits fungicidal activity, particularly against Alternaria which makes it especially useful in growing tomatoes. It also kills nematodes on the soil when applied at 1 Kg/hectare. Its toxicity is quite low, i.e. $LD_{50}$ when applied orally to rats is 1000 mg/Kg. It can be prepared in analogous manner according to Example 22 and has a melting point of 137° C.

All of the foregoing compounds contemplated by the present invention possess the desired selective herbicidal properties, and especially the capability of selectively destroying weeds. It will be realized that the instant compounds possess total herbicidal action when used in large quantities, although selective herbicidal action is obtained when used in smaller quantities. As contemplated herein, the term "weeds" is meant to include not only weeds in the narrow sense, but also in the broad sense, whereby to cover all plants and vegetation considered for the particular purposes in question.

It will be appreciated that the instant specification and examples are set forth by way of illustration and not limitation, and that various modifications and changes may be made without departing from the spirit and scope of the present invention.

What is claimed is:

1. A method for selectively controlling weeds in growing tomatoes which comprises applying to the locus thereof a herbicidally effective amount of a 3-methylthio-4-amino-6-branched butyl-1,2,4-triaqine-5-one having the formula

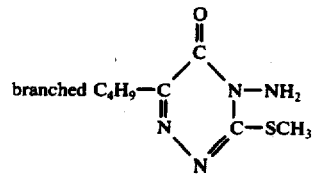

2. A method according to claim 1 wherein branched butyl is tert-butyl.

* * * * *